United States Patent [19]

Jung et al.

[11] Patent Number: 6,024,964
[45] Date of Patent: Feb. 15, 2000

[54] MEMBRANE ANCHOR/ACTIVE COMPOUND CONJUGATE, ITS PREPARATION AND ITS USES

[75] Inventors: Günther Jung; Karl-Heinz Wiesmüller; Jörg Metzger; Hans-Jörg Bühring, all of Tübingen; Gerhard Becker, Ofterdingen; Wolfgang Bessler, Hagelloch, all of Germany

[73] Assignee: Hoechst Aktiengesellschaft, Frankfurt am Main, Germany

[21] Appl. No.: 08/466,695

[22] Filed: Jun. 6, 1995

Related U.S. Application Data

[62] Division of application No. 08/387,624, Feb. 13, 1995, abandoned, which is a continuation of application No. 08/084,091, Jun. 30, 1993, abandoned, which is a continuation-in-part of application No. 07/588,794, Aug. 27, 1990, abandoned, application No. 07/340,833, Apr. 20, 1989, abandoned, and application No. 07/966,603, Oct. 26, 1992, abandoned, which is a continuation of application No. 07/610,222, Nov. 8, 1990, abandoned, said application No. 07/588,794, is a continuation of application No. 07/427,914, Oct. 24, 1989, abandoned, which is a continuation of application No. 07/229,770, Aug. 1, 1988, abandoned, which is a continuation of application No. 06/876,479, Jun. 20, 1986, abandoned.

[30] Foreign Application Priority Data

| Jun. 24, 1985 | [DE] | Germany | 35 22 512 |
| Dec. 27, 1985 | [DE] | Germany | 35 46 150 |
| Apr. 22, 1988 | [DE] | Germany | 38 13 821 |
| Nov. 10, 1989 | [DE] | Germany | 39 37 412 |

[51] Int. Cl.$^7$ .......................... A61K 39/21; A61K 39/02; A61K 39/002; A61K 39/00
[52] U.S. Cl. ................... 424/208.1; 424/234.1; 424/265.1; 424/277.1
[58] Field of Search ............................ 424/208.1, 234.1, 424/265.1, 277.1

[56] References Cited

U.S. PATENT DOCUMENTS

| 4,140,763 | 2/1979 | Bachrach et al. . | |
| 4,401,658 | 8/1983 | Bouchaudon et al. . | |
| 4,439,425 | 3/1984 | Tarcsay et al. | 424/177 |
| 4,459,286 | 7/1984 | Hilleman et al. . | |
| 4,554,101 | 11/1985 | Hopp . | |
| 4,605,512 | 8/1986 | Schaller et al. . | |
| 4,639,512 | 1/1987 | Audibert et al. . | |
| 4,666,886 | 5/1987 | Baschang et al. . | |
| 4,769,237 | 9/1988 | Bittle et al. | 424/88 |
| 5,017,688 | 5/1991 | Gilbert et al. . | |

FOREIGN PATENT DOCUMENTS

| 23745/84 | 1/1984 | Australia . |
| 1 139 305 | 1/1983 | Canada . |
| 0 000 330 | 1/1979 | European Pat. Off. . |
| 0 014 815 | 9/1980 | European Pat. Off. . |
| 0 109 688 | 5/1984 | European Pat. Off. . |
| 0 114 787 | 8/1984 | European Pat. Off. . |
| 0 203 676 | 12/1986 | European Pat. Off. . |
| 0 204 480 | 12/1986 | European Pat. Off. . |
| 0 210 412 | 2/1987 | European Pat. Off. . |
| 0270295 | 6/1988 | European Pat. Off. . |
| 0 338 437 | 10/1989 | European Pat. Off. . |
| 3 546 150 | 1/1987 | Germany . |
| WO 89/02277 | 3/1989 | WIPO . |
| WO 89/07448 | 8/1989 | WIPO . |

OTHER PUBLICATIONS

Haynes, B. F. et al., "Toward an Understanding of the Correlates of Protective Immunity to HIV Infection", *Science*, vol. 271, Jan. 19, 1996, pp. 324–328.
Cohen, J., "Jitters Jeopardize AIDS Vaccine Trials", *Science*, vol. 262, Nov. 12, 1993, pp. 980–981.
Burton, D.R., et al., "Why Do We Not Have An HIV Vaccine and How Can We Make One?", *Nature Medicine Vaccine Supp.*, vol. 4, No. 5, May 1998, pp. 495–498.
(1)Derwent Abstract (C87–009492 secondary accession) Accession No. 87–022868/04.
Australian Patent Abstract, claims 1–3, 14, 23, 24 to AU A–58943/86
Boltz et al. (1988) J. Virol. Methods 22:173–182.
Bessler et al. (1986) Prog. Leukocyte Biol. 5:337–344.
Wiesmuller et al. (Feb. 1989) Vaccines 7:29–33.
Jung et al. (1985) Angew. Chem. Int. Ed. Engl. 24:872–873.
Jung et al. (1984) Synthetic Antigens (Ann. Sclavo) n.2 :191–208.
Jung et al. (1985a) Peptides: Structure Func., Proc. Am. Pep. Sym., ed. C. Derber et al. pp. 27–30.
Jung et al. (1985b) Peptides: Structure and Func., ed. V.J. Hruby et al. pp. 179–182.
Bessler et al. (1985) Immunobiol. 170:239–244.
Wiesmuller et al. (1983) Hoppe–Seyler's Z. Physiol. Chem. Bd. 364,S. 593–606.
Prass et al. (1987) Biochem. Biophys. Acta 900:116–128.
Hummel et al. (1989) Peptides: Proc. Eur. Pept. Symp., 20th Meeting 1988, Ed. G. Jung et al., pp. 686–688.
Krug et al. (1989) Biopolymers 28:499–512.
Reitermann et al. (1989) Biol. Chem. Hoppe–Seyler 370:343–352.

(List continued on next page.)

*Primary Examiner*—Lynette R. F. Smith
*Assistant Examiner*—Brett Nelson
*Attorney, Agent, or Firm*—Finnegan, Henderson, Farabow, Garrett & Dunner, L.L.P.

[57] ABSTRACT

According to certain embodiments, the invention relates to a method of producing antibodies employing an immunoconjugate produced by conjugating at least one membrane-anchoring compound with at least one partial sequence of a viral, bacterial, or protoral protein. The immunoconjugate has the advantage that it can be stored for a very long time even without cooling. According to certain embodiments, the invention relates to an immunoconjugate for the specific induction of cytotoxic T-lymphocytes which comprises a conjugate from at least one membrane anchor compound and a protein, containing at least one killer T-cell epitope, of a virus, a bacterium, a parasite or a tumor antigen, or at least one partial sequence containing at least one killer T-cell epitope of a viral, bacterial or parasite protein or of a tumor antigen.

8 Claims, 16 Drawing Sheets

OTHER PUBLICATIONS

Bodmer et al., "Enhanced Recognition of a Modified Peptide Antigen by Cytotoxic T Cells Specific for Influenza Nucleoprotein," Cell 52:253–258 (1988).

Rothbard et al, "A Sequence Pattern Common to T Cell Epitopes," The EMBO Journal, 7:93–100 (1988).

Deres et al., "In Vivo Priming of Virus–Specific Cytotoxic T Lymphocytes With Synthetic Lipopeptide Vaccine," Nature 342:561–564 (1989).

European Search Report issued in EP 90 12 1189 which is the foreign counterpart of the parent U.S. appln. S.N. 07/966,603.

Wunsch, Angew. Chem. (1971), pp. 773–782.

Rudinger Peptide Hormones, Parsons (ed.), U Park Press, Baltimore, pp. 1–7 (1976).

Chemical Abstracts (108:34506h) 1988.

Surovoy et al., Peptides Proceedings of the Tenth American Peptide Symposium, pp. 553–554 (May 23–28, 1987).

DiMarchi et al., Peptides Proceedings of the Tenth American Peptide Symposium, pp. 531–533 (May 23–28, 1987).

Werner et al., 42 Experientia, pp. 521–531 (1986).

Sela et al., Symposium on Synthetic Peptides as Antigens, pp. 184–199 (London, Jun. 4–6, 1985).

Geysen et al., 82 Proc. Nat'l. Acad. Sci. USA, pp. 178–182 (1985).

European Search Report for European Patent Application EP 86 10 8324.

Boheim et al., Biophysics of Structure and Mechanism, vol. 9, pp. 181–191 (1983).

Schmitt et al., Liebigs Ann. Chem., pp. 321–364 (1985).

Jung et al., Chem. Abstr., vol. 103, No. 176708W (1985).

Schmitt et al., Liebigs Ann. Chem., pp. 345–364 (1985).

Jung et al., Liebigs Ann. Chem., 9: 1608–1622 (1983).

Bessler et al., Chemical Abstracts 101 (23): 701, ref. #211690s (1984).

Johnson et al., Immunobiology 165(1): 27–35 (1983).

Jung et al., Chemical Abstracts 103 (21): 539, ref. #176708w (1985).

Bessler et al., Chemical Abstracts 104 (3), ref. #18419u (1986).

Katoh et al., Nature 329: 654–656 (1986).

European Search Report issued in EP 90 12 1189, which is the foreign counterpart of the parent U.S. appln. S.N. 07/966,603, and English translation.

European Search Report for European Patent Appln EP 86 10 8324, and English translation.

K. Falk O., Rötzschke, S. Stevanovic, G. Jung and H–G. Rammenseé: Allele–Specific Motifs Revealed By Sequencing of Self–Peptides Eluted From MHC Molecules; Nature, vol. 351, pp. 290–296 (1991).

A.R.M. Townsend, J. Rothbard, F.M. Gotch, G. Bahadur, D. Wraith and A. J. McMichael: The Epitopes of Influenza Nucleoprotein Recognized by Cytotoxic T Lymphocytes Can Be Defined With Short Synthetic Peptides; Cell, vol. 44, pp. 959–968 (1986).

I. M. Roitt, J. Brostoff, D.K. Male: Immunologie: DeBoeck Universitè, 3d Edition, pp. 6.11 & 8.5 (1993) & (Not Translation).

I. M. Roitt, J. Brostoff, D.K. Male: Immunology; Mosby, 3d Edition, pp. 6.10–6.13 & 8.4–8.6 (1993).

T. P. Hopp: Immunogenicity Of A Synthetic HBsAg Peptide: Enhancement By Conjungation To A Fatty Acid Carrier; Molecular Immunology, vol. 21, No. 1, pp. 13–16 (1984).

Butini et al., 1994, "Comparative Analysis of HIV–Specific CTL Activity in Lymphoid Tissue and Peripheral Blood", Abstract J306, J. of Cell. Biochem., Suppl. 18B.

Lowell et al., 1988, "Proteosome–Lipopeptide Vaccines: Enhancement of Immunogenicity for Malgica CS Peptides", Science 2401 800–802.

Bessler, et al, "Specific Anhbodies Elicited by . . . " Immunobiology 170:239–244, 1985.

Jung, et al, "Increased Production of . . . " Angew. Chem. Int. Ed. Engl. 24:872–873, 1985.

Lex, et al, 1986, "A Synthetic Analogue of *Escherichia coli* Lipoprotein Tripalmitoyl Pentapeptide Constitutes a Potent Immune Adjuvant." J. Immunol. 137(8):2676–2681.

Jung, et al, 1985, "Enhancement of Immune Response Using B–Lymphocyte Mitogen S Covalently Linked to Antigens." Pept. Structure Funct. Proc. Am. Pep. Symp. Ed. Derber, et al, pp. 27–30.

Gendler, et al, 1988, "A Highly Immunogenic Region of a Human Polymorphic Epithelial Mucin Expressed by Carcinomas is made up of Tandem Repeats.", J. Biol. Chem. 263 (26): 12820–12823.

TAB. 1 ¹³C-NMR SIGNALS OF
a) dioctadecyl maleate
b) S-(1,2-DIOCTADECYLOXYCARBONYLETHYL) -N-palmitoylcysteine tert.-butyl ester
c) S-(1,2-DIOCTADECYLOXYCARBONYLETHYL) -N-palmitoylcysteine
d) S-(1,2-DIOCTADECYLOXYCARBONYLETHYL) -N-palmitoyl-cysteinyl-O-tert.-butyl-seryl-O-tert.-butyl-
   -butyl ester
   seryl-asparaginyl-alanine tert.

a) $CH_3 - CH_2 - CH_2 - (CH_2)_{12} - CH_2 - CH_2 - CH_2 - O - CO - CH$
   $14.1 \quad 22.7 \quad 31.9 \quad 29.2 \quad 25.9 \quad 28.4 \quad 65.4 \quad 165.3 \quad 129.8$
   $29.4$
   $29.7$
   $\qquad \qquad \qquad \qquad \qquad \qquad \qquad \qquad \qquad =$
   $CH_3 - CH_2 - CH_2 - (CH_2)_{12} - CH_2 - CH_2 - CH_2 - O - CO - CH$ b) $CH_3 - CH_2 - CH_2 - (CH_2)_{12} - CH_2 - CH_2 - CH_2 - O - CO - CH_2 \quad 42.1 \quad 42.4$
   $14.1 \quad 22.6 \quad 31.9 \quad 29.2 \quad 25.8 \quad 28.5 \quad 65.3 \quad \qquad \qquad \qquad \quad | \quad |$
   $\qquad \qquad \qquad 29.3 \qquad \qquad \qquad \qquad \qquad \qquad \qquad \quad S \quad 65.7$
   $\qquad \qquad \qquad 29.5 \qquad \qquad \qquad \qquad \qquad \qquad \qquad \quad | \quad -$
   $\qquad \qquad \qquad 29.7 \qquad \qquad \qquad \qquad \qquad \qquad \qquad 170.8 \quad CH_2 \quad 34.3$
   $CH_3 - CH_2 - CH_2 - (CH_2)_{12} - CH_2 - CH_2 - CH_2 - O - CO - CH_2 \quad 170.4 \quad |$
   $\qquad \qquad \qquad \qquad \qquad \qquad \qquad \qquad \qquad \qquad \qquad \qquad 171.6 \quad CH_2$
   $\qquad \qquad \qquad \qquad \qquad \qquad \qquad \qquad \qquad \qquad \qquad \qquad 171.5 \quad |$
   $CH_3 - CH_2 - CH_2 - (CH_2)_{10} - CH_2 - CH_2 - CH_2 - CO - NH - CH - COO - C(CH_3)_3 \quad 27.9$
   $14.1 \quad 22.6 \quad 31.9 \quad 29.2 \quad 25.5 \quad 36.5 \quad 173.8 \qquad \qquad 52.5 \quad 169.4 \quad 82.7$
   $\qquad \qquad \qquad 29.3 \qquad \qquad \qquad 172.9$
   $\qquad \qquad \qquad 29.5$
   $\qquad \qquad \qquad 29.7$

c) CH₃ - CH₂ - CH₂ - (CH₂)₁₂ - CH₂ - CH₂ - CH₂ - O - CO - CH₂   42.3  42.8
   14.1  22.6  31.9  29.3   25.8  28.5  65.5       |
                    29.7                            S        170.7
                                                    |        170.0
                                                   CH₂       171.7   CH₂   33.6
   CH₃ - CH₂ - CH₂ - (CH₂)₁₂ - CH₂ - CH₂ - CH₂ - O - CO - CH   66.0
   14.1  22.6  31.9  29.3   25.8  28.5  65.5
                    29.7
   CH₃ - CH₂ - CH₂ - (CH₂)₁₀ - CH₂ - CH₂ - CO - NH - CH - COOH
                                              52.5  174.5
                                           172.8
                                           172.9                  174.7 d) CH₃ - CH₂ - CH₂ - (CH₂)₁₂ - CH₂ - CH₂ - CH₂ - O - CO - CH₂   43.0
   14.1  22.7  31.9  29.3   25.8  28.5  65.4       |
                    29.7                            S        66.1
                                                    |
                                                   CH₂
   CH₃ - CH₂ - CH₂ - (CH₂)₁₂ - CH₂ - CH₂ - CH₂ - O - CO - CH
   14.1  22.7  31.9  29.3   25.8  28.5  65.4
                    29.7
   CH₃ - CH₂ - CH₂ - (CH₂)₁₀ - CH₂ - CH₂ - CO - NH - CH - CO →
                                        25.6  36.4  51.8

55.0        54.6              50.2          49.1
   -NH - CH - CO - NH - CH - CO - NH - CH - CO - NH - CH - COO - C(CH₃)₃   27.9
   |              |                   |                        |
   CH₂ 60.6     CH₂ 61.0            CH₂ 37.0                  CH₃         81.5
   |              |                                            17.7
   O            O
   |              |
   C(CH₃)₃      C(CH₃)₃            CONH₂
   74.3 27.3    74.3 27.3

CARBONYL SIGNALS (NOT ASSIGNED): 170.0; 170.8; 171.2; 171.5; 171.9; 173.3; 173.6; 173.8

Fig. 6. $^{13}C$ NMR SPECTRUM (J MODULATED SPIN-ECHO SPECTRUM) OF Pam(α-Pam)-Cys-OBu$^t$ (200 mg, 100.62 MHz, 3360 SCANS)

CD Spectrum of HuIFN-(Ly)(11-20)-L-Ala-Aib-Ala-Aib-Ala)₂OMe

MEMBRANE ANCHOR/ACTIVE COMPOUND CONJUGATE, ITS PREPARATION AND ITS USES

This application is a divisional of application Ser. No. 08/387,624, filed Feb. 13, 1995, now abandoned, which is a continuation of Ser. No. 08/084,091, filed Jun. 30, 1993, now abandoned, which is a continuation-in-part of (1) U.S. patent application Ser. No. 07/588,794, filed Sep. 27, 1990, now abandoned, which is a continuation of U.S. patent application Ser. No. 07/427,914, filed Oct. 24, 1989, now abandoned, which is a continuation of U.S. patent application Ser. No. 07/229,770, filed Aug. 1, 1988, now abandoned, which is a continuation of the U.S. patent application Ser. No. 06/876,479, filed Jun. 20, 1986, now abandoned; and (2) a continuation-in-part of U.S. patent application Ser. No. 07/340,833, filed Apr. 20, 1989, now abandoned; and (3) a continuation-in-part of U.S. patent application Ser. No. 07/966,603, filed Oct. 26, 1992, now abandoned, which is a continuation of U.S. patent application Ser. No. 07/610,222, filed Nov. 8, 1990, now abandoned. All of these U.S. patent applications are hereby specifically incorporated by reference herein.

BACKGROUND AND SUMMARY OF THE INVENTION

The invention relates to membrane anchor/active compound conjugates having at least one active compound covalently bonded to the membrane anchor compound(s), to a process for their preparation and to their use. The invention further relates to particularly effective foot and mouth disease (FMD) vaccines which can be prepared using membrane-anchoring compounds and certain partial sequences of the FMD virus. Moreover, the invention also relates to a synthetic vaccine containing membrane anchor/active compound conjugates for the specific induction of cytotoxic T-lymphocytes.

Membrane anchor compounds are compounds which can penetrate into biological and synthetic membranes.

For example, these membrane anchor compounds can be natural membrane lipoproteins as have already been isolated from the outer membrane of *Escherichia coli* and have now also been synthesized. The *E. coli* membrane anchor compound is composed in the N-terminal region of three fatty acids which are bonded to S-glyceryl-l-cysteine (G. Jung et al. in "Peptides, Structure and Function," W. J. Hruby and D. H. Rich, pages 179 to 182, Pierce Chem. Co. Rockford, Ill., 1983).

Moreover, conformation-stabilized alpha-helical polypeptides have already been described for the investigation of biological membranes by means of models, see inter alia alamethicin, an alpha-helical amphiphilic eicosapeptide antibiotic which forms voltage-dependent ionically conducting systems in lipid membranes (Boheim, G., Hanke, W., Jung, G., Biophys. Struct. Mech. 9, pages 181 to 191 (1983); Schmitt, H. and Jung, G., Liebigs Ann. Chem. pages 321 to 344 and 345 to 364 (1985)).

There is a description in European Patent A1-330 of the immunopotentiating action of lipopeptides which are analogs of the lipoprotein from *E. coli* which has been known since 1973. Another European patent application, A2-114787, deals with the ability of lipopeptides of this type to activate alveolar macrophages of rats and mice in vitro so that, after incubation with the substance for 24 hours, the macrophages are able to eliminate tumor cells and, in particular, they significantly increase the production of antibodies, for example against porcine serum albumin.

It is proposed in European Patent A2-114787 to use these lipoprotein derivatives as adjuvants for immunization, that is to say to employ the lipoprotein derivatives of the *E. coli* membrane protein mixed with antigens to improve the immune response.

There is a great need for substances which stimulate and potentiate the immune response, in particular because purified antigens can often be obtained in only minuscule amounts; furthermore, when new batches of antigens are employed there is always the possibility of new contaminants or decomposition products.

It is furthermore desirable not to have to inoculate an experimental animal frequently but, where possible, to obtain the desired immune response by a single dose of the imunogenic material.

Hence it is an object of the present invention to increase the formation of antibodies against antigens or haptens and thus to obtain a specific immunopotentiating action.

According to certain preferred embodiments, the present invention also relates to a vaccine against foot and mouth disease and a process for the preparation thereof.

Foot and mouth disease (FMD) causes great losses in cattle breeding, despite vaccines which have now been available for a long time. One reason for the occurrence of foot and mouth disease at present is the unreliability of classical vaccines which contain killed or inactivated FMD viruses: the inactivation of the virus is occasionally incomplete so that "post-vaccination" outbreaks of FMD may occur (cf. Böhm, Strohmaier, Tierärztl. Umschau 39, 3–8 (1984)). This danger does not exist with synthetic FMD vaccines because in the latter only partial sequences of certain viral proteins, which do not have the function of an intact virus, are used.

Although synthetic FMD vaccines already exist (cf. European Patent Application 0,204,480), they are still in need of improvement.

The present inventors have found that particularly effective FMD vaccines can be prepared using membrane-anchoring compounds and certain partial sequences of the FMD virus. Although the preparation of synthetic vaccines is mentioned in German Offenlegungsschrift DE 3,546,150 A1 as one of many possible uses of membrane anchor/active substance conjugates, it was not to be expected that the conjugates of membrane-anchoring compounds and partial sequences of the FMD virus (membrane anchor/active substance conjugates) would exhibit the exceptional activity which has been found on administration of relatively small amounts of vaccine.

Furthermore, the said vaccines are distinguished, surprisingly, by providing an adequate protection even after a single administration of the vaccine. Moreover, they have the advantage by comparison with conventional vaccines that virtually unlimited storage without cooling is possible.

According to certain preferred embodiments, the invention also relates to a synthetic vaccine for the specific induction of cytotoxic T-lymphocytes.

Cytotoxic T-lymphocytes (killer T-cells) are an essential part of the immune response of warm-blooded animals against intracellular infections. Cytotoxic T-lymphocytes are normally induced only by means of an in vivo vaccination with infectious pathogens (J. Bastin et al., *J. Exp. Med.*, Vol. 165, June 1987). Because of the risks associated with this, a synthetic vaccine for the specific induction of cytotoxic T-lymphocytes would be a substantial improvement. Surprisingly it has now been found that the specific in vivo induction of cytotoxic T-lymphocytes is possible by the use of certain membrane anchor/active compound conjugates containing killer T-cell epitopes.

Although it has been known that membrane anchor/active compound conjugates are suitable for generating neutralizing antibodies (cf. Angew. Chem. 97 (1985), No. 10, p. 883 ff.), a synthetic vaccine containing membrane anchor/active compound conjugates for the specific induction of cytotoxic T-lymphocytes has not yet been reported.

As stated above, it is an object of the present invention to increase the formation of antibodies against antigens or haptens and thus to obtain a specific immunopotentiating action.

The object is achieved according to the invention by the new membrane anchor/active compound conjugate having at least one membrane anchor compound and at least one active compound covalently bonded to the membrane anchor compound(s).

According to the invention, a process for the preparation of membrane anchor compounds is also proposed, which process comprises synthesis of the peptide, which is protected with protective groups in a manner known per se on the functional groups at which no reaction is to take place, by means of known coupling processes on a solid or soluble carrier, such as a polymer (for example Merrifield resin); covalent bonding of the carrier-bound peptides, which have been synthesized in this way, via N-termini or side-groups of the peptide to the membrane anchor compound; isolation of the polymer/peptide conjugate, which has been prepared in this way, by cleavage of the protective groups and the peptide/carrier bond in a manner known per se, and thus the membrane anchor/peptide or the membrane anchor/active compound conjugate being obtained.

The invention also relates to the use of the compounds for the preparation of conventional and monoclonal antibodies in vivo and in vitro; however, it is also possible, in an advantageous manner, to use the compounds according to the invention in genetic engineering to facilitate cell fusion, for the preparation of synthetic vaccines, for the preparation of cell markers with fluorescence labels, spin labels, radioactive labels or the like; for affinity chromatography, in particular for affinity columns; for liposome preparations; as additive to human foodstuffs or animal feeds; and as additive to culture media for microorganisms and, generally, for cell cultures. This may entail, where appropriate, the compounds according to the invention being used, together with vehicles known per se, in solution, ointments, adsorbed onto solid carries, in emulsions or sprays, for purposes in human or veterinary medicine.

According to certain preferred embodiments, the invention also relates to a synthetic vaccine against foot and mouth disease, which vaccine comprises a conjugate of at least one membrane-anchoring compound and at least one partial sequence of a protein of the foot and mouth disease virus.

According to certain preferred embodiments, the invention also relates to a synthetic vaccine for the induction of cytotoxic T-lymphocytes which comprises a conjugate of at least one membrane anchor compound and a protein, containing at least one killer T-cell epitope, of a virus, a bacterium, a parasite or a tumor antigen, or at least one partial sequence containing at least one killer T-cell epitope of a viral, bacterial or parasite protein or of a tumor antigen.

BRIEF DESCRIPTION OF THE DRAWINGS

The figures which are attached to illustrate the invention show:

FIG. 2 the table of the $^{13}C$ NMR spectra;

DETAILED DESCRIPTION OF THE INVENTION

Figure 1:
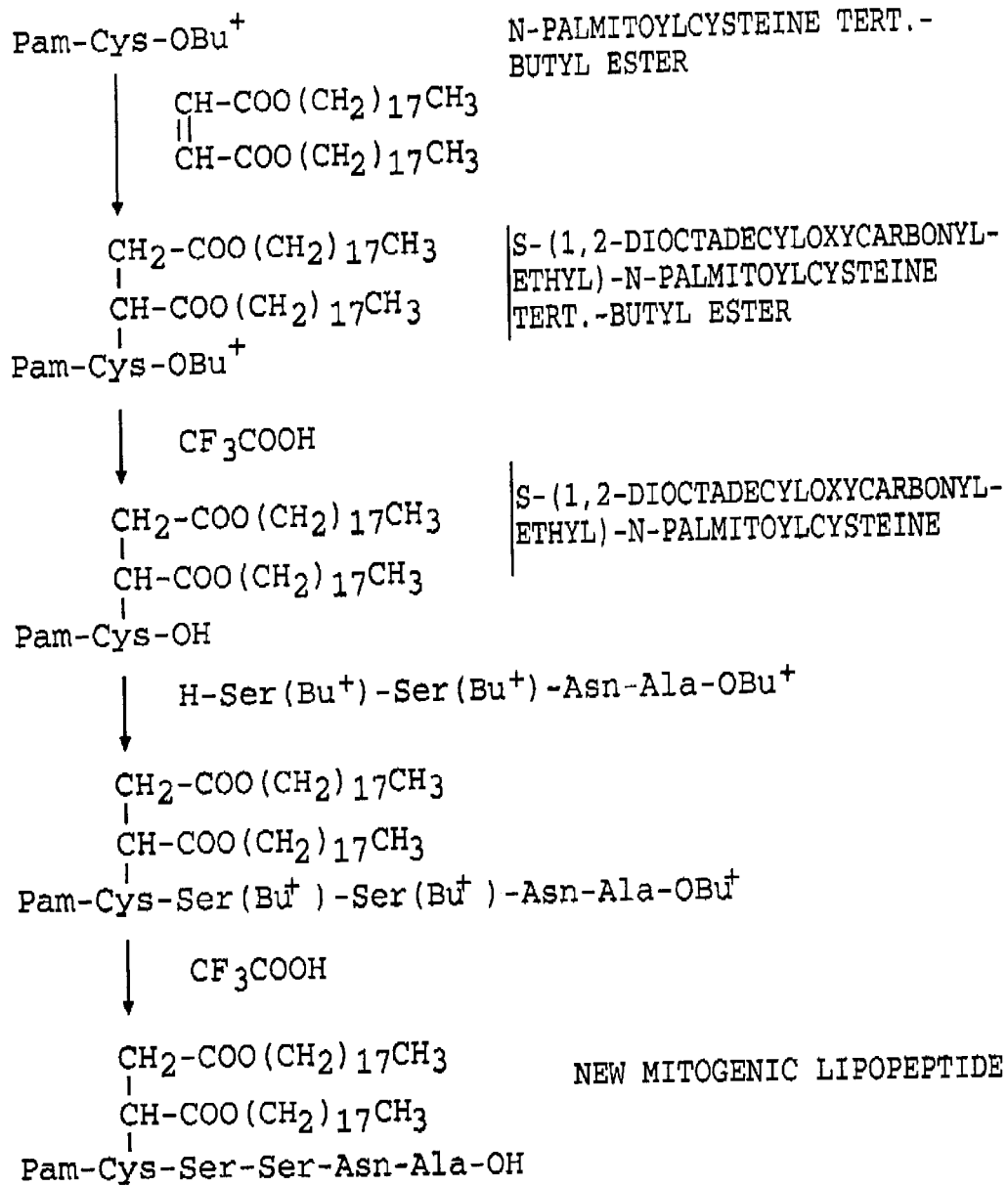
FIG. 1 the scheme for the preparation of Pam-Cys($C_{18}$)$_2$-Ser-Ser-Asn-Ala-Oh.
Figure 3:
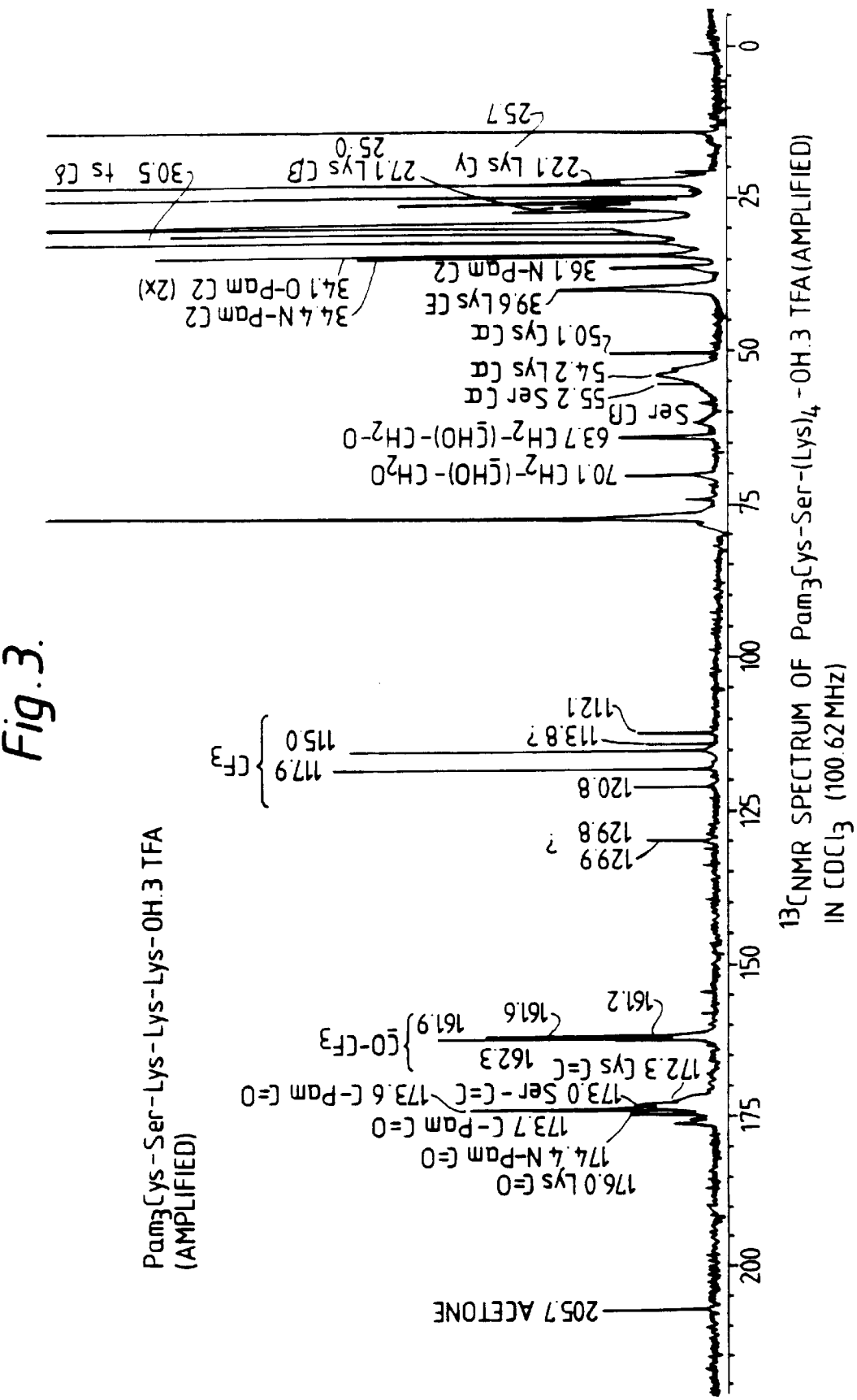
FIG. 3 The $^{13}C$ NMR spectrum of Pam$_3$Cys-Ser-(Lys)$_4$-OH×3TFA in CDCl$_3$.

All the references cited in this application are specifically incorporated by reference herein.

The membrane anchor compound is preferably a compound of one of the following general formulae:

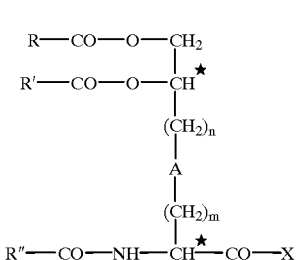

I.

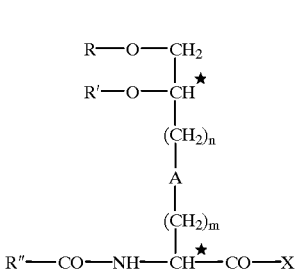

II.

-continued

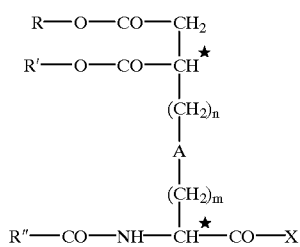

III.

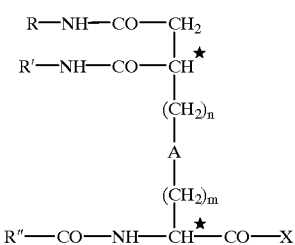

IV.

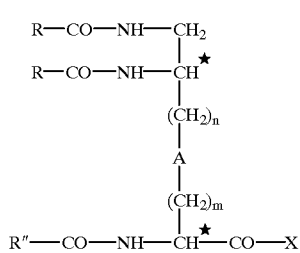

V.

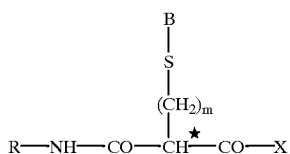

VI.

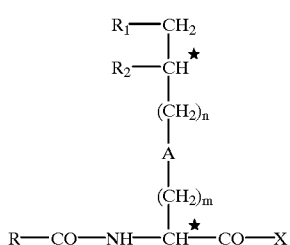

VII.

it being possible for A to be sulfur, oxygen, disulfide (—S—S—), methylene (—CH$_2$—) OR —NH—;

n being 0 to 5; m being 1 or 2; C* being an asymmetric carbon atom with R or S configuration; R, R' and R" being identical or different and being an alkyl, alkenyl or alkynyl group having 7 to 25 carbon atoms or hydrogen, which can optionally be substituted by hydroxyl, amino, oxo, acyl, alkyl or cycloalkyl groups, and R$_1$ and R$_2$ being identical or different and being defined as R, R' and R" or possibly being —OR, —OCOR, —COOR, —NHCOR or —CONHR, and X being an active compound or a spacer-active compound group.

It is also possible, in an advantageous manner, to use a membrane anchor/active compound conjugate according to the invention of the following general formula:

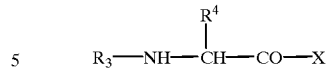

VIII.

R$_3$ being an alpha-acyl-fatty acid residue having between 7 and 25 carbon atoms; preferably between 10 and 20 carbon atoms and very particularly preferably having between 14 and 18 carbon atoms; an alpha-alkyl-beta-hydroxy-fatty acid residue or its beta-hydroxy ester, the ester group being preferably straight-chain or branched chain and having more than 8 carbon atoms, preferably between about 10 and 20 and very particularly preferably between 14 and 18 carbon atoms; it is possible and preferable for formula VIII to be an active compound conjugate with the following membrane anchor compounds: N,N'-diacyllysine; N,N'-diacylornithine; di(monoalkyl)amide or ester of glutamic acid, di(monoalkyl)amide or ester of aspartic acid, N,O-diacyl derivative of serine, homoserine or threonine and N,S-diacyl derivatives of cysteine or homocysteine; serine and homoserine; R$_4$ being a side chain of an amino acid or hydrogen; and X being hydrogen or a spacer-active compound group, it being possible when R$_3$ is a side chain of lysine, ornithine, glutamic acid, aspartic acid or their derivatives for the latter to be bonded, both in the manner of an ester and in the manner of an amide in the same molecule, in alpha or 07 mega positions to R$_4$.

It is particularly preferred for the membrane anchor/active compound conjugates to be prepared by synthesis of the peptide, which is protected with protective groups in a manner known per se on the functional groups at which no reaction is to take place, by means of known coupling processes on a solid or soluble carrier, such as a polymer (for example Merrifield resin); covalent bonding of the carrier-bound peptides, which having been synthesized in this way, via N-termini or side-groups of the peptide to the membrane anchor compound; isolation of the peptide conjugate, which has been prepared in this way, by cleavage of the protective groups and the peptide/carrier bond in a manner known per se, and thus the membrane anchor peptide or the membrane anchor/active compound conjugate being obtained.

The linkage between the peptide and the membrane anchor compound can be produced by condensation, addition, substitution or oxidation (for example, disulfide formation). It is possible to use, in an advantageous manner, conformation-stabilizing alpha-alkylamino acid helices with an alternating amino acid sequence as the membrane anchor, it not being permissible for the alpha-helix to be destabilized by the other amino acids, such as of the type X-(Ala-Aib-Ala-Aib-Ala)$_n$-Y, n being 2 or 4, and X and Y being protective groups which are known per se or —H, —OH or —NH$_2$.

It may be advantageous for the active compound to be covalently linked to two membrane anchor compounds which are, where appropriate, different.

In addition, it is also possible for the active compound to be covalently linked to an adjuvant which is known per se for immunization purposes, such as, for example, muralyl-dipeptide and/or to a lipopolysaccharide.

Examples of active compounds which we propose are: an antigen such as, for example, a low molecular weight partial sequence of a protein or conjugated protein, for example of a glycoprotein, of a viral coat protein, of a bacterial cell wall protein or of a protein of protozoa (antigenic determinant, epitope), an intact protein, an antibiotic, constituents of bacterial membranes, such as muramyldipeptide, lipopolysaccharide, a natural or synthetic hapten, an antibiotic, hormones such as, for example, steroids, a nucleoside, a nucleotide, a nucleic acid, an enzyme, enzyme substrate, an enzyme inhibitor, biotin, avidin, polyethylene glycol, a peptidic active compound such as, for example, tuftsin, polylysine, a fluorescence marker (for example, FITC, RITC, dansyl, luminol or coumarin), a bioluminescence marker, a spin label, an alkaloid, a steroid, biogenic amine, vitamin or even a toxin such as, for example, digoxin, phalloidin, amanitin, tetrodotoxin or the like, a complex-forming agent or a drug.

The nature of the active compound determines the completely novel areas of use which emerge for the substances according to the invention.

It may also be beneficial for several membrane anchor/ active compound conjugate compounds to be crosslinked together in the lipid part and/or active compound part.

The membrane anchor compounds and the active compound can also be connected together via a crosslinker, which results in the active compound becoming more remote from the membrane to which it is attached by the membrane anchor.

Examples of suitable crosslinkers are a dicarboxylic acid or a dicarboxylic acid derivative, diols, diamines, polyethylene glycol, epoxides, maleic acid derivatives or the like.

According to the invention, an unambiguously defined, low molecular weight conjugate which is suitable, inter alia, for immunization and which covalently links together the carrier/antigen/adjuvant principles is prepared. The carrier and adjuvant can be not only a lipopeptide having mitogenic activity, such as, for example, tripalmitoyl-S-glyceryl-cysteine ($Pam_3Cys$) and its analogs such as a $Pam_3Cys$-peptide having from 1 to 10 amino acids, but also lipophilic conformation-stabilized alpha-helices and combinations thereof, such as $Pam_3Cys$-antigen-helix, alpha-helix-antigen-helix or even merely $Pam_3Cys$-antigen or antigen-$Pam_3Cys$ (N- or C-terminal linkage), and antigen-helix or helix-antigen (N- or C-terminal, or incorporated in the helix on side chains of Glu, Lys and the like). Thus, the new compounds differ in essential aspects from all the high molecular weight conjugates of antigens with high molecular weight carrier substances which have hitherto been used, for example proteins, such as serum albumins, globulins or polylysine or, in general, high molecular weight linear or crosslinked polymers.

In particular, however, the new compounds also differ from all hitherto known adjuvants which are merely admixed and, accordingly, do not bring about specific presentation of the antigen on the cell surface. The adjuvants hitherto known have frequently required multiple immunizations and have also resulted in inflammatory reactions in animal experiments. A particular advantage according to the invention is the possibility of reproducible preparation of pyrogen-free, pure, unambiguously chemically defined compounds, and this—in contrast to conventional compounds or mixtures of various substances—also results in an improvement in the reproducibility of antibody formation. Hence, a particular area of use of the compounds according to the invention is viewed as being the area of antibody production, genetic engineering, the preparation of synthetic vaccines, diagnostic methods and therapy in veterinary and human medicine, since the new conjugates have for the first time an action which specifically stimulates the immune response, whereas the adjuvants hitherto used have merely stimulated the immune response non-specifically. Surprisingly, it is even possible with the compounds according to the invention to convert weakly immunogenic compounds into highly immunogenic compounds. Thus, a particular importance of the invention derives from the possibility of dispensing with animal experiments and costs for the preparation of antibodies, since the new immunogens are also highly active in vitro. Moreover, because the immunization method is not inflammatory, an animal can be used several times for obtaining different antibodies.

Finally, it might also be possible to use the new immunogens to prepare polyvalent vaccines, i.e., a membrane anchor to whose side chains several antigens or haptens have been linked so that several different active antibodies can be prepared by means of one immunization.

One example of a water-soluble, mitogenic lipid anchor group is $Pam_3Cys$-Ser$(Lys)_n$-OH, which is particularly suitable for the preparation of the new immunogens as well as for the preparation of fluorescent, radioactive and biologically active cell markers. A particularly desirable property of the membrane anchor/active compound conjugates according to the invention is their amphiphilicity, ie., a partial water-solubility, since in this case it is considerably more straightforward to carry out biological tests on animals and investigations with living cells. Moreover, the artificial lipid bilayer membranes, liposomes and vesicles which are required for some experiments can be prepared, and are stable, only in an aqueous medium.

An example of a suitable amphiphilic, biologically active membrane anchor is $Pam_3Cys$-Ser$(Lys)_n$-OH. The serine residue coupled to $Pam_3Cys$ favors immunogenic properties, whereas the polar, protonted epsilon-amino groups of the lysine residues represent the hydrophilic part of the molecule. Because of its multiple charges, this type of compound has further interesting properties. Owing to induction of interaction between cells, it can be used as a fusion activator in the preparation of hybridoma cells, especially when the lysine chain is relatively long, when coupling to polyethylene glycol, or on covalent incorporation of the biotin/avidin system.

Furthermore, in an advantageous manner, it is possible to use the compounds according to the invention for the preparation of novel liposomes by crosslinking, it being possible for this to take place either in the fatty acid moiety or in the peptide moiety.

The membrane anchor ($Pam_3Cys$ and analogs, and the helices) are also suitable for potentiating the cell/cell interaction when, for example, they are covalently combined with the biotin/avidin system. Other advantageous properties of the compounds according to the invention are that they may facilitate cell fusion as is required, for example, for work in genetic engineering.

Furthermore, the new immunogens can also be used in ELISA, RIA and bioluminescence assays.

Various $Pam_3Cys$ derivatives are lipid- and water-soluble and have potent mitogenic activity in vivo and in vitro. They are also very suitable for labeling of cells with FITC and other markers such as RITC, dansyl and coumarin. In particular, they can also be used for fluorescence microscopy and fluorescence activated cell sorting (FACS).

A reasonably priced membrane anchor having an analogous action to $Pam_3Cys$ is S-(1,2-dioctadecyloxycarbonyl-ethyl)cysteine, whose preparation is described in detail in the experimental part.

Specific coupling of the mitogenically active lipid anchors to antigens can also be effected by crosslinkers, such as, for example, with dicarboxylic acid monohydrazide derivatives of the general formula:

X—NH—NH—CO—A—CO—B—Y or

X—NH—NH—CO—A—COOH where A and B are amino acid or $(CH_2)_n$, and X and Y are protective groups known per se.

It is also possible to use every other suitable crosslinker or spacer for the preparation of the new substances, a particularly preferred embodiment of the invention always being represented by the principle (low molecular weight carrier and adjuvant)-(antigen) as long as it contains lipopeptide structures with lipid membrane anchor functions and/or conformation-stabilized helices.

Particularly advantageous effects can be found by use of the compounds according to the invention in affinity chromatography, for which purpose lipopeptide-antigen (hapten) conjugates are particularly suitable. The latter are outstandingly suitable for loading conventional reversed phase HPLC columns (or preparation RP columns), this entailing, for example, anchoring of a tripalmitoyl compound, which has been applied in organic aqueous systems, in the apolar alkyl layer. The presentation of the antigen to the mobile aqueous phase remains the same as on cell surfaces, and thus it invites adsorption of the antibodies. Hence, it is possible to enrich or isolate antibodies, which specifically react with the relevant antigen, from dilute serum directly on an affinity column of this type. The elution of the antibodies is effected as with other affinity columns, for example by adjusting the pH.

According to certain preferred embodiments, the invention also relates to a synthetic vaccine against foot and mouth disease, which vaccine comprises a conjugate of at least one membrane-anchoring compound and at least one partial sequence of a protein of the foot and mouth disease virus.

As described above, membrane-anchoring compounds are compounds which can be embedded in biological or synthetic membranes.

Further information on membrane-anchoring compounds is found in the German Offenlegungsschrift 3,546,150 and in G. Jung et al. in "Peptides, Structure and Function," already cited.

Preferred membrane anchor/active substance conjugates are those in which a membrane-anchoring compound and an active substance, i.e., a partial sequence of foot and mouth disease (FMD) virus, are linked together covalently.

Particularly suitable membrane anchor/active substance conjugates for use in synthetic vaccines have proved to be those in which the membrane-anchoring compound is a lipoprotein. very particularly suitable are membrane-anchoring compounds of the following formulae

I.

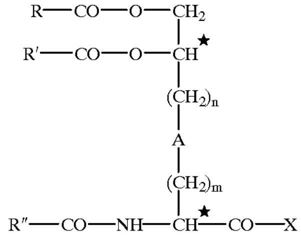

-continued

II.

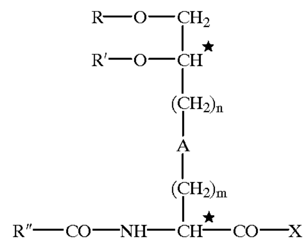

III.

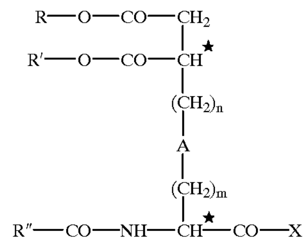

IV.

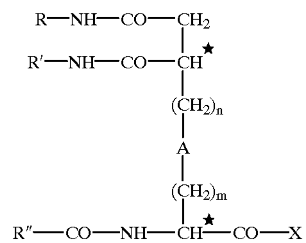

V.

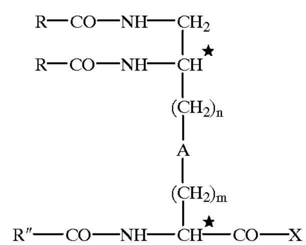

VI.

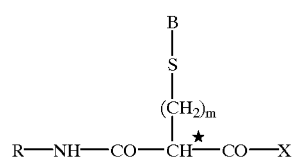

VII.

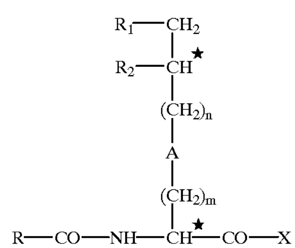

in which A can be sulfur, oxygen, disulfide (—S—S—), methylene ($—CH_2—$) or —NH—;

n=0 to 5, m=1 or 2;

C* is an asymmetric carbon atom with the R or S configuration, R, R' and R" are identical or different and each is hydrogen or an alkyl, alkenyl or alkynyl group which has 7 to 25 carbon atoms and which can be substituted by hydroxyl, amino, oxo, acyl, alkyl or cycloalkyl groups, B in formula VI can have the meaning of each of the —(CH$_2$)$_n$-(substituted alkyl) radicals listed in formulae I–V, and R$_1$ and R$_2$ are identical or different and have the same meanings as R, R' and R" but can also be —OR, —O—COR, —COOR, NHCOR or —CONHR, where X is a chain of 1 to 10 amino acids to which the partial sequence of the virus is bonded.

Examples of these to be particularly emphasized are: N-termini occurring in bacterial lipoprotein, such as, for example: Y-Ser-Ser-Ser-Asn, Y-Ile-Leu-Leu-Ala, Y-Ale-Asn-Asn-Gln, Y-Asn-Ser-Asn-Ser, Y-Gly-Ala-Met-Ser, Y-Gln-Ala-Asn-Tyr, Y-Gln-Val-Asn-Asn, Y-Asp-Asn-Ser-Ser, where Y can be one of the radicals listed under formula I to VII. These lipopentapeptides can also be used in shortened form (lipodi, lipotri or lipotetrapeptides) as membrane-anchoring compounds. Very particularly preferred is N-palmitoyl-S-[2,3-(bispalmitoyloxy)propyl]-cysteinyl-seryl-serine (Pam$_3$Cys-Ser-Ser), N-palmitoyl-S-[2,3-(bispalmitoyloxy)propyl]-cysteinyl-seryl-glycine and N-palmitoyl-S-[2,3-(bispalmitoyloxy)propyl]-cysteinyl-alanyl-D-isoglutamine. Examples of other preferred membrane-anchoring compounds are to be found in German Offenlegungsschrift 3,546,150.

Many different partial sequences can be employed as the partial sequences of the FMD virus which are bonded to the membrane-anchoring compound. The following partial sequences are preferred:

| | |
|---|---|
| Partial sequence | -(134–154) |
| " | -(135–154) |
| " | -(134–158) |
| " | -(134–160) |
| " | -(141–160) |
| Partial sequence | -(141–158) |
| " | -(200–213) |
| " | -(200–210) |
| " | -(161–180) | it being possible to use the sequences of all known serotypes and subtypes. Examples of serotypes which may be indicated in this connection are:

| Serotype A: | 134 160 |
|---|---|
| A$_5$ Westerwald | NKYSTGGP--RRGDMGSAAARAAKQLP |
| | 161 180 |
| | ASFNYGAIRAITIHELLVRM |
| | 200 213 |
| | RHKQKIIAPARQLL |
| A$_{12}$ USA | 134 160 |
| | NKYSASGSG-VRGDFGSLAPRVARQLP |
| | 161 180 |
| | ASFNYGAIKAETIHELLVRM |
| | 200 212 |
| | RHKQKIIAPGKQL |

-continued

| Serotype C: | 134 160 |
|---|---|
| C$_1$ Oberbayern | TTY TAST ----RGDLAHLTAT RAGHLP |
| | 161 180 |
| | TSFNFGAUKAETITGLLVAM |
| | 200 213 |
| | RHKQPLVAPAKQLL |
| Serotype O: | 134 160 |
| o$_1$ Kaufbeuren: | CRYNRNAVPNLRGDLQVLAQKVARTLP |
| O$_1$ Lausanne: | CRYSRNAVPNLRGDLQVLAQKVARTLP |
| O$_2$ Normandy: | RRYSRNAVPNVRGDLQALGQKARTLP |
| O Wuppertal: | CLYSDARVSNVRGDLQVLAQKAERAL |
| O Israel: | CRYGNVAVTNVRGDLQVLAQKAERALP |
| | 200 213 |
| 01 Kaufbeuren: | RHKQKIVAPVKQTL |
| | 161 180 |
| 01 Kaufbeuren: | TSFNYGAIKATRVTELLYRM |

Particularly suitable synthetic vaccines are those which are composed of a mixture of peptides from various sero- and/or subtypes of the foot and mouth disease virus, each of which is covalently bonded to the membrane-anchoring compound (s).

Particularly preferred synthetic vaccines are those which are composed of a mixture of sequences VP1 134–160 of serotypes O, A and C, bonded to the membrane-anchoring compound N-palmitoyl-S-[2,3-(bispalmitoyloxy)propyl]-cysteinyl-seryl-serine.

When the sequence 134–154 from serotype O and the sequence 134–155 from serotype A are used, the latter can, as long as it contains C-terminal lysine, be linked covalently via the ε-amino group to the membrane-anchoring compound.

Particularly suitable synthetic vaccines according to the invention have proved to be those which contain the partial sequence of FMD virus VP 1 (135–154).

Additionally, particularly preferred is a vaccine composed of N-palmitoyl-S-[2,3-(bispalmitoyloxy)propyl]-cysteinyl-seryl-seryl-VP 1 (135–154), i.e., the compound of the formula below.

[Figure: Structure showing membrane-anchoring lipopeptide conjugated to FMD virus peptide sequence (residues 135-154): Arg-Ser-Ser-... with amino acids Tyr, Asn, Ala, Asn, Asp, Val, Ser, Asn, Gly, Leu, Leu, Arg, Pro, Val, Leu, Ala, Arg, Gln, Gln, Lys]

The membrane-anchoring compounds can, in principle, be in the form of R,S or R,R diastereomers or of a mixture of diastereomers. However, it has emerged that the vaccines which contain an R,R-diastereomeric, membrane-anchoring compound have particularly high activity.

The invention additionally relates to a process for the preparation of a synthetic vaccine, which comprises bonding partial sequences of the FMD virus by a conjugation reaction to the membrane-anchoring compound. The conjugation reaction can be, for example, a condensation, addition, substitution, oxidation or disulfide formation. Preferred conjugation methods are indicated in Example 1. Further conjugation methods are described in German Offenlegungsschrift 3,546,150 which has already been cited.

The preparation of the membrane-anchoring compounds is likewise described in detail in the last-mentioned German Offenlegungsschrift.

The separation of the diastereomers, which is necessary where appropriate, can also be carried out by a variety of methods as described, for example, in Hoppe-Seyler's Z. Physiolog. Chem. 364 (1983) 593. A preferred separation process is described in Example 2.

The partial sequences of the particular FMD proteins can be constructed in a variety of ways known from the literature, cf., for example, Wünsch et al. in Houben-Weyl, vol. 15/1,2, Stuttgart; Thieme-Verlag or Wünsch in Angew. Chem. 83 (1971), 773, E. Gross and J. Meienhofer (editors); The Peptides, vol. 1 (1979), 2 (1979), 3 (1981) and 5 (1983), Academic Press, New York; or German Offenlegungsscrift 3,546,150. A preferred process for the preparation of a partial sequence and of a conjugate is explained in more detail in Example 3.

The invention additionally relates to pharmaceutical or veterinary medical foundations which contain a conjugate of membrane-anchoring compound and partial sequence of a FMD virus. Besides a solvent, there is normally no additional need for additional auxiliaries and carriers or adjuvants for the formulations according to the invention. However, in some cases, it may be worthwhile to add such auxiliaries and/or carriers as well as, where appropriate, adjuvants to the formulations according to the invention. The relevant substances are mixed and dispensed by processes known to those skilled in the art.

The amount of vaccine necessary for reliable immunization of an animal depends on the species, on the membrane-anchoring compound(s) and on the partial sequence(s) of the FMD virus and should be determined empirically in the individual case. For example, sufficient for reliable immunization of a guinea pig against FMD virus serotype $O_1K$ is a single administration of about 100–500 μg of vaccine according to the invention, without further auxiliaries or carriers.

The invention additionally relates to the use of the described vaccine for raising antibodies in mammals.

According to certain preferred embodiments, the invention also relates to a synthetic vaccine for the induction of cytotoxic T-lymphocytes which comprises a conjugate of at least one membrane anchor compound and a protein, containing at least one killer T-cell epitope, of a virus, a bacterium, a parasite or a tumor antigen, or at least one partial sequence containing at least one killer T-cell epitope of a viral, bacterial or parasite protein or of a tumor antigen.

The said membrane anchor compound preferably is a bacterial lipoprotein. A compound of the formulae below is particularly preferred as membrane anchor compound

I.

$$\begin{array}{l} R\text{—CO—O—}CH_2 \\ R'\text{—CO—O—}CH^* \\ \phantom{R'\text{—CO—O—}}(CH_2)_n \\ \phantom{R'\text{—CO—O—}}A \\ \phantom{R'\text{—CO—O—}}(CH_2)_m \\ R''\text{—CO—NH—}CH^*\text{—CO—X} \end{array}$$

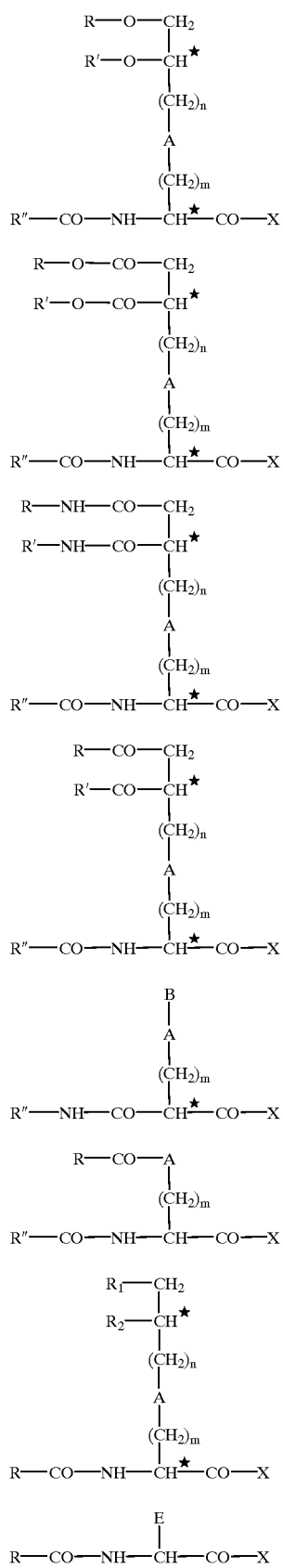

in which A may be sulfur, oxygen, disulfide (—S—S—), methylene (—CH$_2$—) or —NH—;

n=0 to 5, m=1 or 2;

C* is an asymmetric carbon atom with an R- or S-configuration, R, R' and R" are identical or different and are hydrogen or an alkyl, alkenyl or alkynyl group having 7 to 25 carbon atoms, which can be substituted with hydroxyl, amino, oxo, acyl, alkyl or cycloalkyl groups, E in formula IX can be hydrogen or any desired side chain of a natural or artificial α-amino acid, B in formula VI can have the meaning of each of the —(CH$_2$)$_n$-(substituted alkyl) radicals listed in the formulae I–V, and R$_1$ and R$_2$ are identical or different and have the same meanings as R, R' and R" but can also be —OR, —O—COR, —COOR, —NHCOR or —CONHR, where X is a chain of up to 10 amino acids to which the protein or the partial sequence of the viral, bacterial or parasite protein or of a tumor antigen is bonded, or is the protein or the partial sequence itself.

Examples of these which may be pointed out especially are: N-termini which are present in bacterial lipoprotein, such as, for example: Y-Ser-Ser-Ser-Asn, Y-Ile-Leu-Leu-Ala, Y-Ala-Asn-Asn-Gln, Y-Asn-Ser-Asn-Ser, Y-Gly-Ala-Met-Ser, Y-Gln-Ala-Asn-Tyr, Y-Gln-Val-Asn-Asn, Y-Asp-Asn-Ser-Ser, where Y can be one of the radicals listed under formula I to VII. Short forms (lipodipeptides, lipotripeptides or lipotetrapeptides) of these lipopentapeptides can also be used as membrane anchor compound. N-Pal-mitoyl-S-[2,3 (bispalmitoyloxy)propyl]-cysteinyl-seryl-serine (Pam$_3$Cys-Ser-Ser), N-palmitoyl-S-[2,3(bispalmitoyloxy)propyl]-cysteinyl-seryl-glycine and N-palmitoyl-S-[2,3(bispalmitoyloxy)propyl]-cysteinyl-alanyl-D-isoglutamine are very particularly preferred.

Further compounds which are particularly preferred are compounds of the formulae I and III, in particular compounds of the formula I.

The substituent A is preferred to be sulfur or methylene; sulfur is particularly preferred.

The substituents R, R' and R" are preferred to be alkyl radicals having 14 to 18 C atoms; alkyl radicals having 16 C atoms are particularly preferred.

The substituent X is preferred to be composed of 1 to 2 polar amino acid residues, the serine residue being particularly preferred.

Various proteins or partial protein sequences of pathogens which appear intracellularly or of viral, bacterial or parasite proteins or of tumor antigens which are recognized by killer T-cells, are suitable for the coupling to the membrane anchor compound for the vaccine according to the invention.

Such proteins or partial sequences (also referred to as killer T-cell epitopes) are distinguished by the fact that, together with MHC molecules (major histocompatibility complex), they are recognized by cytotoxic T-lymphocytes.

The vaccine according to the invention is suitable for the immunization against all pathogens which have killer T-cell epitopes, such as, for example, against adenoviruses, HIV, influenza viruses, LCMV, MCMV, hepatitis viruses, HTLV, FELV, *Treponema palladium, gonococcus, Bordetella pertussis, plasmodia, listeria, mycobacteria* or *leishmania*. Killer T-cell epitopes which have been known previously are the partial sequences listed in the table below, the influenza nucleoprotein P$_3$CSS-NP 147–158 (R$^-$) and the HIV epitopes occupying a special position.

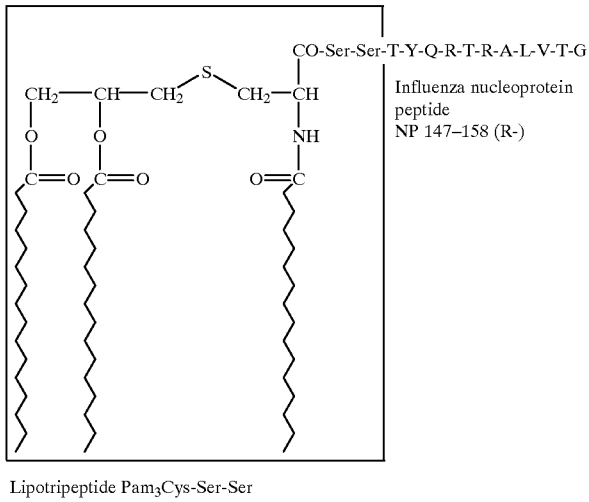

Lipotripeptide Pam3Cys-Ser-Ser

| Organism | Protein | From–To | Restr. | Sequence |
|---|---|---|---|---|
| Adenovirus Ad5E1A | — | — | — | Db PSNTPPEI |
| HIV | env (gp 120) | 381–392 | HLA A2 | (K)NCGGEFFYCNS |
| HIV | env (gp 120) | 308–322 | Dd | RIQRGPGRAFVTIGK |
| HIV | env (gp 120) | 410–429 | DR4 | GSDTITLPCRIKQFINMWQE |
| HIV | gag (p17) | 418–443 | A2 | KEGHQMKDCTERQANF |
| HIV | gag (p17) | 446–460 | A2 | GNFLQSRPEPTAPPA |
| HIV | gag (p24) | 193–203 | A2 | GHQAAMEKLKE |
| HIV | gag (p24) | 219–233 | A2 | HAGPLAPGQMREPRG |
| HIV | gag (p24) | 265–280 | B27 | KRWIILGLNKIVRMYC |
| Influenza | Nucleoprotein | 82–94 | HLA A2 | MVVKLGEFYNQMM |
| Influenza | Matrix | 57–68 | HLA A2 | KGILGFVFTLTV |
| Influenza | Nucleoprotein | 335–349 | B37 B44 A2 Aw69 | SAAFEDLRVLSFIRG |
| Influenza | Hemagglutinin H3 | 58–73 | H-2 Ad | ILDGIDCTLIDALLGD |
| Influenza | Hemagglutinin H3 | 58–73 | H-2 Ad | ILDGIDCTLIDALLGD |
| Influenza | Hemagglutinin | 181–204 103–123 | H-2K;H-2K | — |
| Influenza | Nucleoprotein | 365–379 |  | SDYEGRLIQNSLTI |
| Influenza | Nucleoprotein | 335–349 | H-2b | LASNENMETMESSTL |
| Influenza | Nucleoprotein | 384–393 | HLA B27 | RYWAIRTRSG |
| Influenza A/NT/60/68 | Nucleoprotein | 147–158 | Kd | TYQRTRALV(R)TG |
| LCMV | Nucleoprotein | 118–126 | Ld Lq | RPQASGVYM |
| LCMV | — | 278–286 | H-2b | VENPGGYCL |
| — | — | 277–293 | H-2b | GVENPGGYCLTKWMILA |
| — | — | 168–176 | — | YPHFMPTNL |
| MCMV | — | 161–179 | Ld | GRLMYDMYPHFMPTNLGPS |
| P815 | Tumor antigen P91A | 12–24 | Ld | ISTQNHRALDLVA |
| Plasmodium falciparum | Circumsporozoite prot. | 368–390 | H-2K | KPKDELDYENDIEKKICKMEKCSC |
| berghei | " | 249–260 | Kd | NDDSYIPSAEKI |
| yoelii | — | 276–288 | Kd | NEDSYVPSAEQI |
| Hepatitis | B | HBSAg | 21–28 | — PLGFFPDH |

With the aid of the vaccine according to the invention it is, moreover, possible to mix various membrane anchor compounds coupled to various partial sequences in order to obtain a vaccine which is optimally adapted to a particular target. Furthermore, the corresponding mixture can additionally contain membrane anchor/active compound conjugates which stimulate the humoral immune response and additionally lead to the production of neutralizing antibodies (Vaccine 7, 29–33 (1989), Angew. Chem., Int. Ed. 24, 872–873 (1989)). Moreover, it is also possible to couple various partial sequences covalently and combine them with a membrane anchor compound.

The invention furthermore relates to a process for the preparation of a synthetic vaccine which comprises bonding proteins or partial sequences of pathogens to the membrane anchor compound by a conjugating reaction. The conjugating reaction can, for example, be a condensation, addition, substitution, oxidation or disulfide formation. Conjugating methods which are preferred are shown in the examples. Further conjugating methods are described in the German Offenlegungsschrift 3,546,150 quoted above.

The preparation of membrane anchor compounds is likewise described in detail in the last-mentioned German Offenlegungsschrift.

The separation of diastereomers which may be necessary can be carried out by various methods as, for example, described in Hoppe-Seyler's Z. Physiolog. Chem. 364 (1983) 593.

The synthesis of the partial sequences to be employed in the membrane anchor/active compound conjugates can be carried out in various ways known from the literature, cf., for example, Wünsch et al. in Houben-Weyl, vol. 15/1.2, Stuttgart; Thieme-Verlag or Wünsch in Angew. Chem. 83 (1971); E. Gross and J. Meienhofer (eds.), The Peptides, vol. 1 (1979), 2 (1979), 3 (1981) and 5 (1983) Academic Press, New York 7713; or the German Offenlegungschrift 3,546,150. A preferred method for the preparation of a partial sequence and a conjugate is illustrated in more detail in Example 5.

Furthermore, the invention relates to pharmaceutical preparations or preparations for veterinary medicine which contain conjugates of at least one membrane anchor compound and at least one partial sequence of one of the proteins or organisms mentioned. Normally no additional auxiliaries and excipients or adjuvants are needed for the preparations according to the invention in addition to a solvent. However, it can be sensible in some cases to add auxiliaries and/or excipients of this type and, if desired, adjuvants to the preparations according to the invention (Anton Mayr, Gerhard Eißnen, Barbara Mayr-Bibrack, Handbuch der Schutzimpfungen in der Tiermedizin (Handbook of Vaccines in Veterinary Medicine), 1984, Verlag Paul Parey, Berlin-Hamburg).

The amount of vaccine which is necessary for a safe immunization of a warm-blooded animal depends on the species of warm-blooded animal, on the membrane anchor compound(s) and protein or the partial sequence(s) of the organism, immunity to which it is intended, and has to be determined empirically in each individual case.

The intention now is to illustrate below the invention in detail by means of examples. First, the abbreviations used in Examples I–XX, and Example A are listed:
  Aib=2-methylalanine
  TFA=trifluoroacetic acid
  EGF R=epidermal growth factor receptor
  Pam=palmitoyl radical
  DCC=dicyclohexylcarbodiimide
  DMF=dimethylformamide
  FITC=fluorescein isothiocyanate
  Fmoc=fluorenylmethoxycarbonyl
  But=tert.-butyl radical
  PS—DVB=styreneldivinylbenzene copolymer with 4-(hydroxymethyl)phenoxymethyl anchor groups
  HOBt=1-hydroxybenzotriazole
  RITC=rhodamine isothiocyanate
  Hu IFN-(Ly) 11–20=antigenic determinant of human interferon
  DCH=Dicyclohexylurea
  EE=Ethylacetate Examples I–XX describe some preparation processes for substances according to the invention and their precursors:

I. Preparation of Pam$_3$Cys-Ser-EGF-R (516–529)

After the customary stepwise synthesis (Merrifield synthesis protecting with N α-Fmoc/(But), with DCC/HOBt and symmetric anhydrides) of the EGF-R segment (526–529), the final amino acid attached was Fmoc-Ser (But)—OH. After elimination of the Fmoc group with piperidine/DMF (1:1, 15 min), the resin-bound pentacapeptide of EGF-R H-Ser-(But)-Asn-Leu-Leu-Glu-(OBut)-Gly-Glu(OBut)-Pro-Arg(H$^+$)-Glu-(OBut)-Phe-Val-Glu(OBut)-Asn-Ser(But)-O-p-alkoxybenzyl-copoly (divinylbenzene/styrene) (1 g, loading 0.5 mmol/g) was linked with Pam-Cys(CH$_2$—CH(OPam)CH$_2$(OPam)) (2 mmol, in DMF/CH$_2$Cl$_2$ (1:1)) and DCC/HOBt (2 mmol, preactivated at 0° C. for 20 min) (16 h), followed by a second coupling (4 h). The 36lipohexadecapeptide was cleaved off with trifluoroacetic acid (5 ml) with the addition of thioanisole (0.25 ml) within 2 h.
Yield:
  960 mg=(76%) Pam-Cys(CH$_2$—CH(OPam)CH$_2$(OPam)) Ser-Asn-Leu-Leu-Glu-Gly-Glu-Pro-Arg-Glu-Phe-Val-Glu-Asn-Ser-OH×CF$_3$COOH (correct amino acid analysis, no racemization).

II. Preparation of S-(1,2-dioctadecyloxycarbonylethyl)-N-palmitoyl-L(or D) cysteine tert.-butyl ester Dioctadecyl maleate can be obtained by the general procedure for esterifications of maleic acid (H. Klostergaard, J. Org. Chem. 23 (1958), 108).
$^{13}$C NMR spectrum:
  See FIG. 2.
1.2 mmol (500 mg) of N-palmitoyl-L-cysteine tert.-butyl ester and 1.2 mmol (745 mg) of dioctadecyl maleate are dissolved in 20 ml of THF. After addition of 20 mmol (3 ml) of N,N,N',N'-tetramethylethylenediamine, the mixture is stirred under nitrogen with a reflux condenser for 12 h. After addition of 100 ml of methanol and 5 ml-of water, the colorless precipitate is filtered off with suction, washed with water and methanol and dried in vacuo over P$_2$O$_5$.
Yield: 1 g (83%)
Melting point:
  51 degrees Celsius
Thin-layer chromatography:
  R$_y$=0.80; (mobile phase: CHCl$_3$/ethyl acetate=14:1)
$^{13}$C NMR:
  See FIG. 2.
Molecular weight:
  C$_{63}$H$_{113}$NO$_7$S (1035.7)
Elemental analysis:
  Calculated C 72.99 H 11.76 N 1.35 S 3.09; Found C 73.08 H 11.92 N 1.27 S 3.27

III. Preparation of S-(1,2-dioctadecyloxycarbonylethyl)-N-nalmitoylcysteine 0.48 mmol (500 mg) of the t-butyl ester described under II is stirred in 65.3 mmol (7.45 g, 5 ml) of trifluoroacetic acid in a closed vessel at room temperature for 1 h. The mixture is evaporated in a rotary evaporator under high vacuum, the residue is taken up in 1 ml of chloroform, 50 ml of petroleum ether is added precipitate at −20 degrees C., and the product is dried in vacuo over P$_2$O$_5$.
Yield:
  420 mg (89%)
Melting point:
  64 degrees Celsius
Thin-layer chromatography on silica gel plates:
  R$_F$=0.73; (mobile phase: CHCl$_3$/MeOH/H$_2$O=65:25:4)
$^{13}$C NMR:
  See Tab. 1.
Molecular weight:
  C59H$_{113}$NO$_7$S (980.6)
Elemental analysis:
  Calculated: C 72.27 H 11.62 N 1.43 S 3.27; Found: C 72.46 H 11.75 N 1.36 S 3.50

The new cysteine derivative and its t-butyl ester can be separated into the diastereomers on silica gel and RP chromatography. It is thus possible to prepare the two pairs of diastereomers of the L- and D-cysteine derivative.

IV. Preparation of S-(1,2-dioctadecyloxycarbonylethyl)-N-palmitoyl-Cys-Ser (But-Ser(But)-Asn-Ala-OBut 0.2 mmol (196 mg) of S-1,2-dioctadecyloxycarbonylethyl)-N-palmitoylcysteine is dissolved in 5 ml of dichloromethane, and preactivation is carried out with 0.2 mol (27 mg) of HOBt in 0.5 ml of DMF and 0.2 mmol (41 mg ) of DCC by stirring at 0 degrees C. for 30 min.

After addition of 0.2 mmol (109 mg) of H-Ser(But)-Ser (But)-Asn-Ala-OBut in 3 ml of dichloromethane, the mixture is stirred at room temperature for 12 h. Without further working up 40 ml of methanol are added to the reaction mixture. The colorless product can be filtered off with suction after 3 h. It is taken up in a little dichloromethane and again precipitated with methanol. After washing with methanol, it is dried in vacuo over $P_2O_5$.

Yield:
260 mg (86%)
Melting point:
194 degrees Celsius
Thin-layer chromatography:
$R_F$=0.95; (mobile phase: $CHCl_3/MeOH/H_2O$=65:25:4)
$R_F$=0.70; (mobile phase: $CHCl_3$/MeOH/glacial acetic acid=90:10:1)
$^{13}C$ NMR:
See FIG. 2.
Molecular weight:
$C_{84}H_{158}N_6O_{14}S$ (1508.3)
Elemental analysis:
Calculated: C 66.89 H 10.56 N 5.57; Found: C 67.10 H 10.41 N 5.52

V. Preparation of S-(1,2-dioctadecyloxycarbonylethyl)-N-palmitoyl-Cys-Ser-Ser-Asn-Ala 53 μmol (80 mg) of protected lipopeptide (IV) are stirred with 13 mmol (1.5 g; 1 ml) of trifluoroacetic acid in a closed vessel at room temperature for 1 h. After evaporation under high vacuum, the residue is taken up twice with 10 ml of dichloromethane each time and evaporated each time in a rotary evaporator. The residue is taken up in 3 ml of chloroform and precipitated with 5 ml of methanol at 4 degrees Celsius in 12 h. The product is filtered off with suction, washed with methanol and dried in a desiccator over $P_2O_5$.

Yield:
63 mg (87%)
melting point:
208 degrees Celsius (decomposition)
Thin-layer chromatography:
$R_F$=0.63; (mobile phase: $CHCl_3$/MeOH/glacial acetic acid/$H_2O$=64:25:3:4)
$R_F$=0.55; (mobile phase: $CHCl_3/MeOH/H_2O$=64:25:4)
$R_F$=0.06; (mobile phase: $CHCl_3$/MeOH/glacial acetic acid=90:10:1)
Amino acid analysis:
Cysteic acid 0.6; aspartic acid 0.93; serine 1.8; alanine 1.0.
Molecular weight:
$C_{72}H_{134}N_6O_{14}S$ (1340)

VI. Preparation of Pam3Cys-Ser-(Lvs )4-OH

Pam3Cys-Ser(Lys)4-OH was synthesized by the solid-phase method (MERRIFIELD) on a p-alkoxybenzyl alcohol/PS-DVB (1%) copolymer with N-Fmoc-amino acids and acid-labile side-chain protection (But for serine and Boc for lysine). The symmetric anhydrides of the Fmoc-amino acids were used. The coupling to Pam3Cys-OH was carried out by the DCC/HOBt method and repeated in order to achieve as near quantitative conversion as possible. In order to cleave the lipopeptide off the carrier resin and to remove the side-chain protection, the resin was treated twice with trifluoroacetic acid for 1.5 h and the acid was then removed in a rotary evaporator under high vacuum. The product was recrystallized from acetone.

The elemental analysis and the $^{13}C$ spectrum indicates that the lipopeptide is in the form of the trifluoroacetate. Assuming that Pam3Cys-Ser-(Lys)4-OH is in the form of a zwitterion, there are still three ε-amino groups remaining which can be protonated by three trifluoroacetic acid molecules.

The $^{13}C$ NMR spectrum of Pam Cys-Ser-(Lys)4-OH×3 TFA shows that the compound is in the form of the trifluoroacetate. (Quartet of the $CF_3$ group at 110–120 ppm, and carbonyl signals at 161–162 ppm). Owing to the aggregation of the polar part of the molecule, the lines for the Lys. and Ser carbon atoms are greatly broadened. The carbonyl signal at 206.9 ppm is produced by acetone which was used for the recrystallization and which is still adherent.

Molecular weight:
1510.4
Elemental analysis:
Calculated: C 56.40 H 8.70 N 7.56 S 1.73; Found C 55.58 H 9.33 N 6.54 S 2.61
Amino acid analysis:
The amino acid analysis showed that the ratio of serine to lysine is 1:4.2. The characteristic decomposition products of S-glycerylcysteine produced during the hydrolysis (6 N HCl, 110° C., 18 h) were present (comparison with known standards). The peptide content was calculated to be 83%. 3 TFA molecules per lipopeptide correspond to a peptide content of 80.2%, which agrees well with the analysis.

VII. Preparation of Pam3Cys-Ser-(Lys)4-OH×3 TFA

VII.1. Coupiling of Fmoc-Lys(Boc)-OH to the carrier resin

Fmoc-Lys(Boc)-OH (4.5 g, 9.6-mmol) in 15 to 20 ml of DMF/$CH_2Cl_2$ 1:1 (v/v) at 0 degrees C. is mixed with DCC (0.99 g, 4.8 mmol). After 30 min, the precipitated urea is removed by filtration directly into a shaker vessel which contains p-benzyloxybenzyl alcohol resin (2.5 g, 1.6 mmol of OH groups). After addition of pyridine (0.39 ml, 4.8 mmol), the mixture is Shaken at room temperature for 18 h. The solvent is removed by filtration with suction, and the resin is washed 3 times each with 20 ml of DMF/$CH_2Cl_2$ and DMF for each time. The resin is added to 20 ml of $CH_2Cl_2$ and then mixed first with pyridine (28.8 mmol, 6 equivalents) and then with benzoyl-chloride (28.8 mmol, 6 eqivalents). The mixture is shaken at room temperature for 1 h. The solvent is removed by filtration with suction, and the resin is washed 3 times each with 20 ml of $CH_2Cl_2$, DMF, isopropanol and PE 30/50.

VII.2. Symmetric Fmoc-amino acid anhydride

Fmoc-Lys(Boc)-OH (4.5 g, 9.6 mmol, 3 equivalents) is dissolved in 15 ml of $CH_2Cl_2$/DMF and, at 0 degrees Celsius, DCC (4.8 mmol, 1.5 equivalents) is added. After 30 min at 0 degrees Celsius, the urea is removed by filtration directly into the reactor and the process is continued as indicated in the table below.

The following procedure applies to ⅕ of the amount of resin used at the start (0.5 g, 0.32 mmol) of OH groups).

Fmoc-O-butyl-serine (0.74 g, 1.91 mmol) is dissolved in 4 ml of $Ch_2Cl_2$/DMF and, at 0 degrees Celsius, DCC (0.96 mmol) is added.

TABLE

Sequential synthesis of the peptide using symmetric Fmoc-amino acid anhydrides

| Operation | Reagent | Time [min] | Number of times |
|---|---|---|---|
| 1 | $CH_2Cl_2$ | 2 | 2 |
| 2 | DMF | 2 | 2 |
| 3 | 55% piperidine/DMF (v/v) | 5 | 1 |
| 4 | 55% piperidine/DMF (v/v) | 10 | 1 |
| 5 | DMF | 2 | 3 |
| 6 | isopropanol | 5 | 2 |
| 7 | DMF | 2 | 3 |
| 8 | $CH_2Cl_2$ | 2 | 3 |
| 9 | DMF | 2 | 2 |
| 10 | Coupling with 3 eq. of symmetric Fmoc-amino acid anhydride in DMF/$CH_2Cl_2$ 1:1 (v:v); after 15 min addition of 3 eq. of NMM | | |
| 11 | DMF | 2 | 3 |
| 12 | $CH_2Cl_2$ | 2 | 3 |
| 13 | Completeness of coupling checked by the Kaiser test; steps 10–12 repeated if necessary | | |
| 14 | Acetylation: 2 eq. of $Ac_2O$ and 0.5 eq. of NMM in 20 ml of $CH_2Cl_2$ | 15 | 1 |
| 15 | $CH_2Cl_2$ | 2 | 3 |
| 16 | isopropanol | 2 | 3 |
| 17 | $CH_2Cl_2$ | 2 | 3 |

After 30 min, the urea is removed by filtration at 0 degrees C. directly into the reactor, and the procedure is continued as usual.

VII.3. Coupling to $Pam_3Cys$—OH $Pam_3Cys$—OH (0.58 g, 0.64 mmol) is dissolved in 5 ml of $CH_2Cl_2$/DMF 1:1 (v:v) and, at 0 C. degrees, is mixed with HOBt (93 mg, 0.64 mmol) and DCC (0.64 mmol). After 30 min at 0 C. degrees, the mixture is poured directly into the reactor. After shaking tor 16 h, a second coupling is carried out, with the same molar ratios as above, for 4 h. The solvent is removed by filtration pith suction, and the resin is washed 3 times each with 20 ml of DMF/$CH_2Cl_2$ and DMF.

VII.4. Cleavage of the hexapeptide from the polymer

The Boc-protected peptide/polymer resin compound (about 1 g) from VII.3 is thoroughly washed with $CH_2Cl_2$ and shaken 2×1.5 h with a mixture of 5 m of TFA and 0.5 m of anisole. The filtrate is evaporated in vacuo, and the residue is taken up in 5 ml of $CHCl_3$. $Pam_3Cys$-Ser-(Lys)$_4$-OH×3TFA crystallizes out after addition of 50 ml of acetone at −20 degrees Celsius, is removed by centrifugation and is dried under high vacuum.

Yield:
0.41 g (85%)

Melting point:
205 degrees Celsius (decomposition)

Thin-layer chromatography on silica gel plates:
$R_F$=0.42; (mobile phase: n-BuOH/pyridine/$H_2O$/glacial acetic acid=4:1:1:2)
$R_F$=0.82; (mobile phase: n-BuOH/MeOH/$H_2O$/glacial acetic acid=10:4:10:6)

Amino acid analysis:
Ser 0.95 (1); Lys 4 (4)

Molecular weight:
$C_{87}H_{159}N_{10}O_{19}SF_9$ (1852.6)

Elemental analysis:
Calculated: C 56.40 H 8.70 N 7.56 S 1.73; Found: C 55.58 H 9.33 N 6.94 S 2.61

VIII. Preparation of $Pam_3Cys$-Ser-(Lys)$_4$-OH-FITC×2 TFA

Fluoresceine isothiocyanate (3.9 mg, 10 micromol) is dissolved in 2 ml of chloroform and added to a solution of $Pam_3Cys$-Ser-(Lys)$_4$-OH×3TFA (18.5 mg, 10 micromol) in 2 ml of chloroform. After addition of 4-methylmorpho-line (10 microliters, 10 micromol), the mixture is stirred for 1 h and the solvent is then removed in a rotary evaporator. The residue is dissolved in 10 ml of chloroform/acetone 1:1. The yellow product forms a voluminous precipitate at −20 degrees Celsius and is removed by centrifugation and dried under high vacuum.

Yield:
16 mg after purification on SEPHADEX LH 20. The product is in the form of the trifluoroacetate and fluoresces very strongly on excitation with UV light of wavelength 366 nm. Compared with the starting material, a-amino group is covalently linked with FITC. This results in the molecular formula $Pam_3Cys$-Ser-(Lys)$_4$-OH-FITC×2TFA, assuming the zwitterionic structure is retained.

Molecular weight:
$C_{106}H_{169}N_{11}O_{22}S_2F_6$ (2127.68)

Thin-layer chromatography on silica gel plates:
$R_F$=0.72; (mobile phase: n-butanol/pyridine/water/glacial acetic acid=4:1:1:2)
$R_F$=0.73; (mobile phase: n-butanol/formic acid/water=7:4:2)

Amino acid analysis:
Ser 1.11 (1.00) Lys 4.00 (4.00)
The hydrolysis products of glycerylcysteine are present.

IX. Preparation of $Pam_3Cys$-Ser-(Lys)$_4$-OH×3HCl $Pam_3Cys$-Ser-(Lys)$_4$-OH×3TFA (185.2 mg, 0.1 mmol) is just dissolved in a little chloroform, and approximately the same volume of ethereal HCl solution is added. The mixture is thoroughly shaken, whereupon there is some precipitation but the major part remains in solution. The mixture is evaporated to dryness in a rotary evaporator and ether/HCl is added once more. After this procedure has been repeated several times, the residue is dissolved in a little chloroform, and acetone is added until the solution becomes cloudy. The product crystallizes as a colorless powder at −20 degrees C and is filtered off with suction and dried under high vacuum.

Yield:
153 mg

Molecular weight:
$C_{81}H_{159}N_{10}O_{13}SCl_3$ (1619, 63)

Elemental analysis:
Calculated: C 60.07 H 9.89 N 8.65; Found: C 57.64 H 11.20 N 8.39
Excess HCl is still adherent to the product.

Field-desorption mass spectrometry:
The M$^+$ peak appears at m/e 1510, together with M$^+$+1 and M$^+$+2. The protonated fragments $Pam_3Cys$—NH (908.5) at m/e 909, 910, 911 and 912 are characteristic.

X. N,S-Dipalmitoylcysteine tert.-butyl ester

Figure 4:
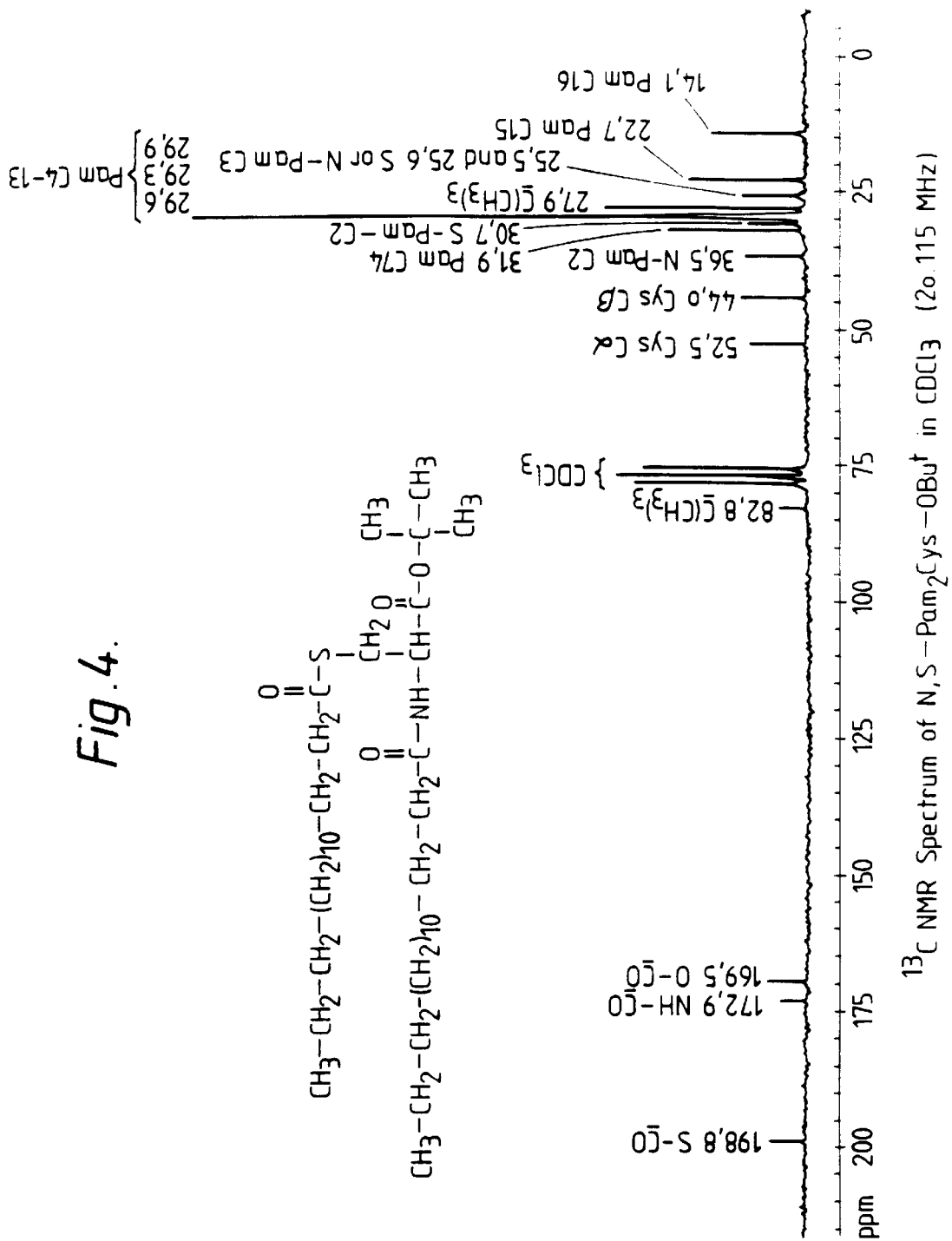
FIG. 4 the $^{13}C$ NMR spectrum of Pam-Cys(Pam)-OBut in CDCl$_3$.

Palmitic acid (2.5 g, 9.6 mmol), dimethylaminopyridine (130 mg, 0.9 mmol) and dicyclohexylcarbodiimide (9.6 mmol) are dissolved in 100 ml of chloroform. The solution is stirred for half an hour and N-palmitoylcysteine tert.-butyl ester (2 g, 4.8 mmol), which has previously been dissolved in 50 ml of chloroform, is added dropwise to the other solution. After 1½ h, the solvent is removed in a rotary evaporator, and the residue is taken up in 100 ml of chloroform/methanol 1:5. The product forms a voluminous precipitate at −20 degrees C. It is filtered off with suction and dried under high vacuum.
Yield:
2.3 g (73%)
Molecular weight: (mass spectrometers)
$C_{39}H_{75}NO_4S$ (655.20)
Elemental analysis:
Calculated: C 71.48 H 11.71 N 2.13 S 4.89; Found: C 71.72 H 12.14 N 2.12 S 4.77
Thin-layer chromatoaraphy on silica gel plates:
$R_F$=(mobile phase: chloroform/ethyl acetate 95:5)
$R_F$=(mobile phase: chloroform/cyclohexane/MeOH 10:7:1)
$^{13}C$ NMR:
See FIG. 4.

II. N-(α-Tetradecyl-β-hydroxyoctadecanoy)cysteine tert.-butyl ester

N-(α-Palmitoylpalmitoyl)cysteine tert.-butyl ester (1.5 g, 2.3 mmol) is dissolved in 10 ml of i-propanol, and 1.5 times the molar amount of sodium borohydride is added. The mixture is stirred for two h, and after completion of the reaction, nitrogen-saturated 1 N hydrochloric acid is added until there is no further evolution of hydrogen. This results in a voluminous precipitate of the product. It is filtered off with suction, washed several times with nitrogen-saturated water and dried under high vacuum.
Yield:
1.4 g (93%)
Molecular weight: (determined from the mass spectrum)
$C_{39}H_{77}NO_4S$=656.11
Thin-layer chromatography on silica gel plates:
$R_F$=0.84 (mobile phase: chloroform/ethyl acetate 95:5)
Elemental analysis:
Calculated: C 71.39 H 11.83 N 2.13 S 4.89; Found: C 71.32 H 12.39 N 2.04 S 5.33

XII. N-(α-Tetradecyl-β-hydroxyoctadecanoyl) cysteine

N-(α-Tetradecyl-β-hydroxyoctadecanoyl)cysteine tert.-butyl ester (1 g, 1.5 mmol) is treated with anhydrous trifluoroacetic acid for ½ h, and the latter is then removed in a rotary evaporator under high vacuum. The residue is dissolved in tert.-butanol and is freeze-dried.
Field:
0.7 g (78%)
Molecular weight: (determined from the mass spectrum)
$C_{35}H_{69}NO_4S$ (600.0)
Elemental analysis:
Calculated: C 70.06 H 10.92 N 2.33 S 5.34; Found: C 70.36 H 10.44 N 2.45 S 5.01
Thin-layer chromatography on silica gel plates:
$R_F$=0.43; (mobile phase: chloroform/methanol/water 65:25:4)

XIII. N,S-Dipalmitoylcyoteine

Figure 5:
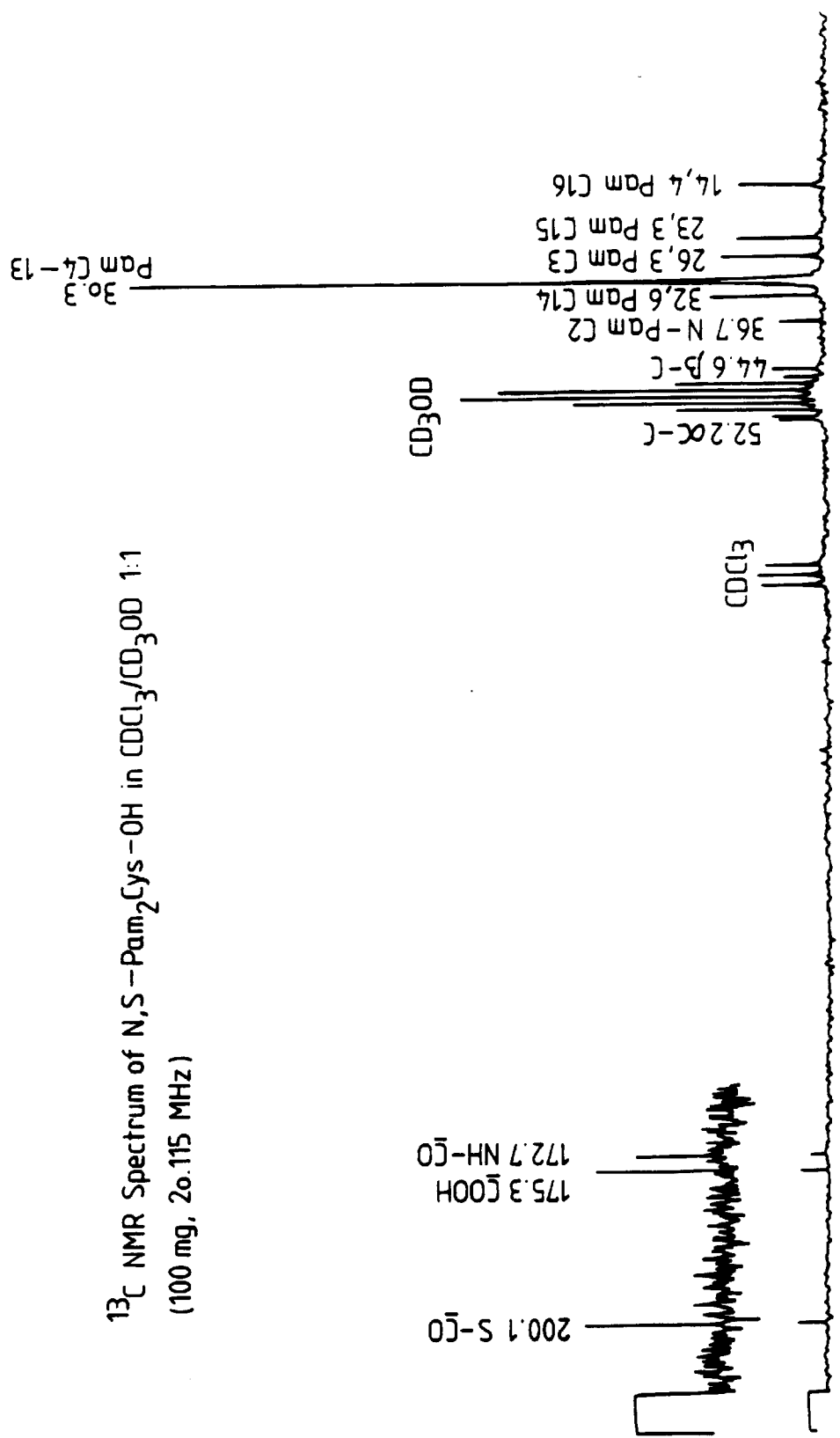
FIG. 5 the $^{13}C$ NMR spectrum of Pam-Cys(Pam)-OH in CDCl$_3$/CD$_3$OD 1:1.
Figure 6:
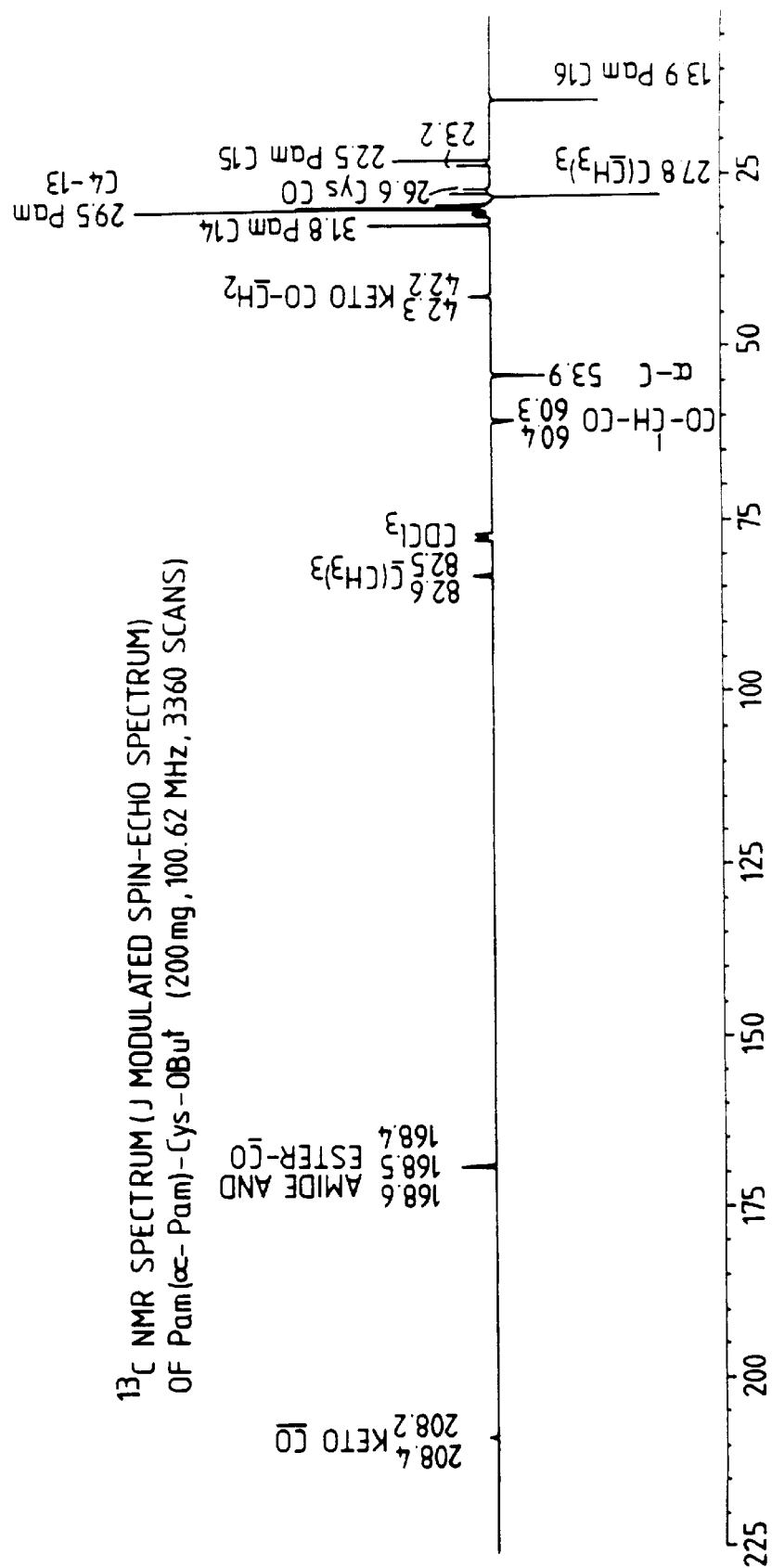
FIG. 6 the $^{13}C$ NMR spectrum (J-modulated spin-echo spectrum) of Pam($\alpha$-Pam)Cys-OBut.
Figure 7:
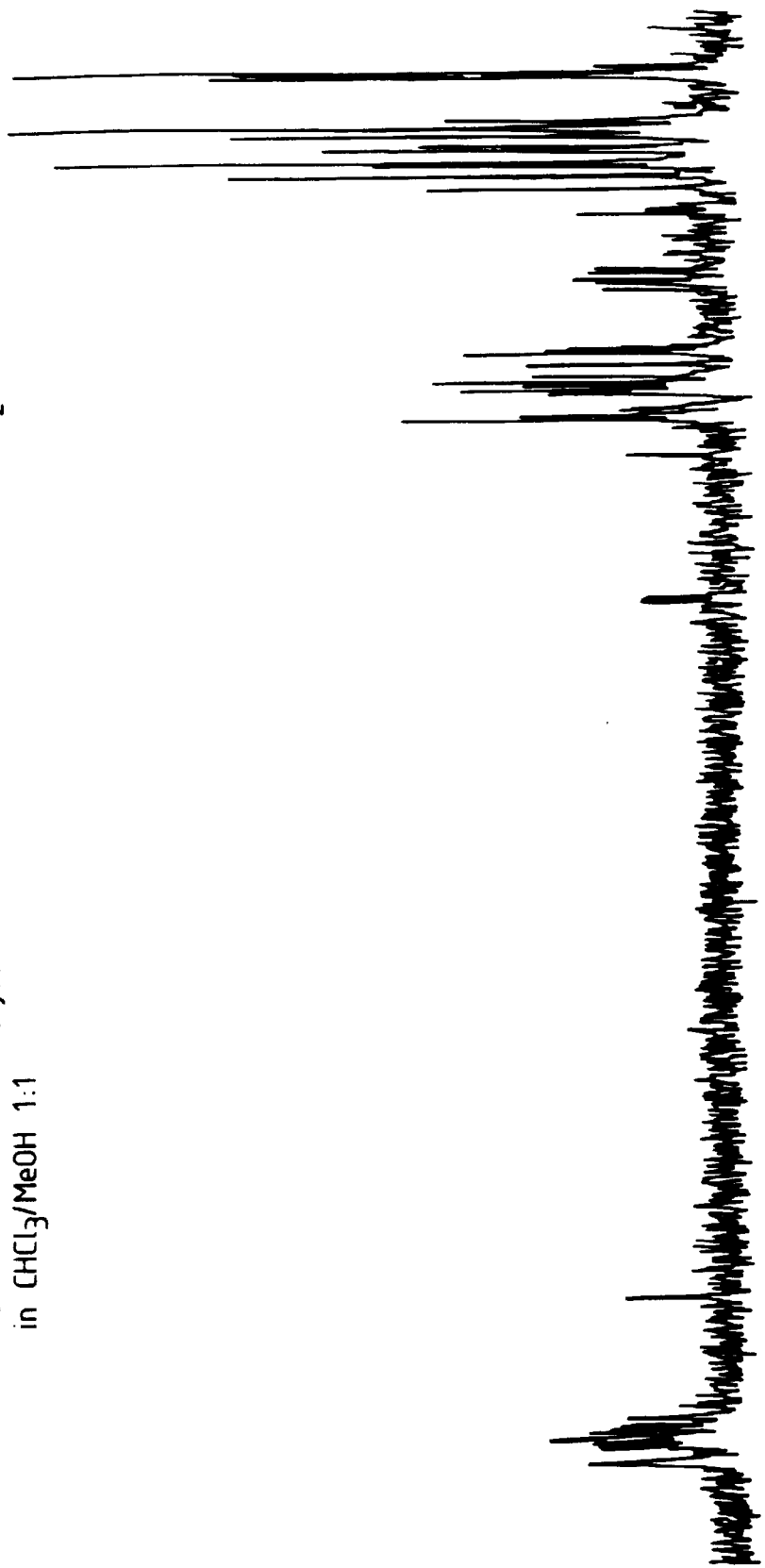
FIG. 7 the $^{13}C$ NMR (100 MHz) of the alpha-helix.
Figure 8:
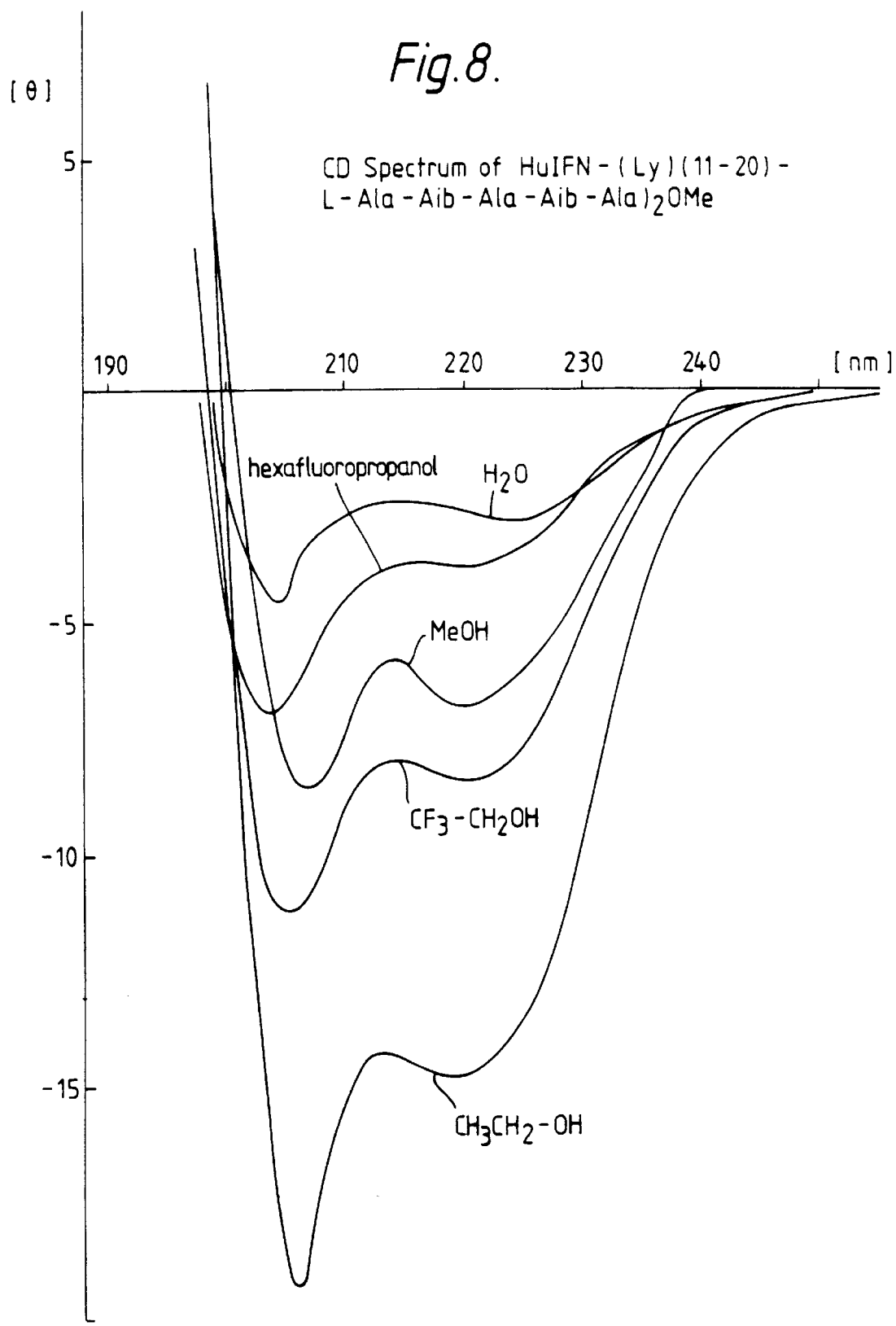
FIG. 8 the CD spectrum of the alpha-helix of HuIFN-($\alpha$-Ly)-11–20.

N,S-Dipalmitoylcysteine tert.-butyl ester (1 g, 1.5 mmol) is treated with anhydrous trifluoroacetic acid for 1 h. The latter is then removed in a rotary evaporator under high vacuum, and the residue is taken up in tert.-butanol and freeze-dried.
Yield:
0.8 g (89%)
Molecular weight: (determined from the mass snectrum)
$C_{35}H_{67}NO_4S$ (598.00)
Elemental analysis:
Calculated: C 70.18 H 11.44 N 2.34 S 5.34; Found: C 69.97 H 11.31 N 2.50 S 5.17
Thin-layer chromatography:
$R_F$=0.30; (mobile phase: chloroform/methanol/glacial acetic acid 90:10:1)
$R_F$=0.75; (mobile phase: chloroform/methanol/water 65:25:4)
$R_F$=0.81; (mobile phase: chloroform/methanol/ammonia (25%)/ water 65:25:3:4)
$^{13}C$ NMR:
See FIG. 5.

XIV. N-(α-Palmitoaypalmitoyl)-N'-palmitoylcysteine di-tert.-butyl ester

Palmitoyl chloride (8 g, 30 mmol) is dissolved in 40 ml of nitrogen-saturated dimethylformamide, and triethylamine (60 ml, 60 mmol) is added. The mixture is stirred under reflux in a stream of nitrogen for three h, during which the triethylammonium chloride which is produced in the formation of the tetradecylketene dimer precipitates out as a colorless salt. The reflux condenser is then replaced by a dropping funnel, and a solution of cysteine di-tert.-butyl ester (4.9 g, 15 mmol) in 20 ml of dimethylformamide is slowly added dropwise. After 6 hs, the solvent is removed in a rotary evaporator, and the residue is taken up in chloroform and washed twice with 100 ml of 5% strength potassium bisulfate solution each time and once with 1,200 ml of water. The organic phase is dried over anhydrous sodium sulfate, and the solvent is removed once more. At −20 degrees Celsius a mixture of N-(α-palmitoylpalmitoyl)-N'-palmitoylcysteine tert.-butyl ester and N,N'-dipalmitoylcysteine di-tert.-butyl ester crystallizes out and the products are separated by gel filtration on SEPHADEX LH-20 in chloroform/methanol 1:1.
Yield:
6.4 g (40%)
Molecular weight: (mass spectrum)
$C_{62}H_{118}N_2O_7S$ (1067.76)
Thin-layer chromatography on silica gel plates:
$R_F$=0.69; (mobile phase: chloroform/ethyl acetate 91:5)

XV. N-(α-Palmitoylpalmitoyl)cysteine tert.-butyl ester

N-(α-Palmitoylpalmitoyl)-N'-palmitoylcysteine di-tert.-butyl ester (3.2 g, 3 mmol) is dissolved in a little methylene chloride, and 100 ml of 9.1 N methanolic hydrochloric acid are added. The solution is transferred into an electrolysis cell with a silver electrode as anode and mercury as cathode, and is reduced at a constant voltage of −1.1 V. The current falls from about 200 mA to almost zero at the end of the electrochemical reduction. The solvent is then removed in a rotary evaporator, and the mixture of products comprising N-(α-palmitoylpalmitoryl)cysteine tert.-butyl ester and N-palmitoylcysteine tert.-butyl ester is precipitated from methanol at −20 degrees Celsius. These two compounds are separated by gel filtration on SEPHADEX LH-20 in chloroform/methanol 1:1.
Yield:
1.5 g (76%)
Molecular weight: (determined from the mass spectrum)
$C_{39}H_{75}NO_4S$ (654.09)
Thin-layer chromatography on silica gel plates:
$R_F$=0.75; (mobile phase: chloroform/ethyl acetate 95:5)

Elemental analysis:
Calculated: C 71.48 H 11.71 N 2.13 S 4.89; Found: C 71.16 H 11.31 N 2.00 S 4.65

XVI. Preparation of an Antigen Conjugate with a Conformation-stabilized α-Helical Membrane Anchor Synthesis of HuIFN-α(Ly)(11-20)-(L-Ala-Aib-Ala-Aib-Ala)$_2$-Ome, a 20-peptide which has on the N-terminal end an antigenic determinant of human interferon (α(Ly)).

The synthesis of the lipophilic membrane anchor with a functional amino group at the end, H-(Ala-Aib-Ala-Aib-Ala)$_2$-OMe, can be applied to other conjugates. The alpha-helix can also be extended once or twice by the Ala-Aib-Ala-Aib-Ala unit. It is advantageous for this purpose to start from the pentapeptide Boc-Ala-Aib-L-Ala-Aib-L-Ala-OMe. (R. Oekonomopulos, G. Jung, Liebigs Ann. Chem. 1979, 1151; H. Schmitt, W. Winter, R. Bosch, G. Jung, Liebig Ann. Chem. 1982, 1304).

XVII. Predration of Boc-Asn-Arg(NO$_2$)-Arg(NO$_2$)—CH

XVII.1. Boc-Arg(NO$_2$)-OMe

Boc-Arg(NO$_2$)-OMe (15.97 g, 50 mmol) and HOBt (6.67 g, 50 mmol) in DMF (100 ml) were added at −10 degrees Celsius to HClxH-Arg(NO$_2$)-oMe (13.49 g, 50 mmol) and NMM (5.5 ml, 50 mmol) in CH$_2$Cl$_2$ (12 mol) and the mixture was stirred at −10 degrees Celsius for 30 min, at 0 degrees Celsius for 1 h and at room temperature for 3 h. The reaction was then stopped with a few drops of glacial acetic acid. The precipitated DCU was removed by filtration, and the solvent was removed under high vacuum. The oily residue was dissolved in ethyl acetate with the addition of a little n-butanol. After the organic phase had been washed with 5% KHSO$_4$ solution, 5% KHCO$_3$ solution and saturated NaCl solution, it was dried over Na$_2$So$_4$, and petroleum ether (30–50) was added and the mixture was cooled to precipitate.
Yield:
20.30 g (76%)
Melting point:
130 degrees Celsius (decomposition)
Thin-layer chromatography:
R$_F$(I)=0.69,
R$_F$(II)=0.87,
R$_F$(III)=0.81,
R$_F$(IV)=0.32,
R$_F$(V)=0.42
Molecular weight determination:
C$_{18}$H$_{54}$N$_{10}$O$_9$ (534.5)
Elemental analysis:
Calculated: C 40.45 H 6.41 N 26.20; Found: C 40.39 H 6.55 N 26.11

XVII.2. HClxH-Arg(NO$_2$)-Arg(NO$_2$)-OMe

Boc-Arg-(NO$_2$)-Arg(NO$_2$)-OMe (20.00 g, 37.42 mmol) was mixed with 1.2 N HCl/acetic acid (110 ml) and, after 30 min, the mixture was poured into stirred ether (600 ml). This resulted in precipitation of HClxH-Arg(NO$_2$)-Arg-(NO$_2$)-OMe which was pure by thin-layer chromatography.
Yield:
17.3 g (98%)
Thin-layer chromatography on silica gel plates:
R$_F$(I)=0.37,
R$_F$(II)=0.29,
R$_F$(III)=0.44,
R$_F$(IV)=0.07,
R$_F$(V)=0.10

XVII.3. Boc-Asn-Arg(NO$_2$)-Arg(NO$_2$)-OMe

Boc-Asn—OH (8.39 g, 36.10 mmol) and HOBt (4.89 g, 36.10 mmol) in DMF (75 ml) were added at −10° C. to HClxH-Arg(NO$_2$)-Arg(NO$_2$)-OMe (17.00 g, 36.10 mmol) and NMM (3.98 mmol) in DMF (75 ml). After addition of DCC (7.53 g, 36.50 mmol) in CH$_2$Cl$_2$ (10 ml), the mixture was stirred at −10 degrees Celsius for 30 min, at 0 degrees Celsius for 1 h and at room temperature for 3 h. After the reaction had been stopped with a few drops of glacial acetic acid, the solvent was removed by evaporation in vacuo, and the residue was taken up in a little methanol. This solution was added dropwise to stirred dry ether. The residue was removed by filtration and taken up in methanol. The pure product precipitated out in the cold.
Yield:
18.25 g (78%)
Melting point:
170 degrees Celsius
Thin-layer chromatography:
R$_F$(I)=0.59,
R$_F$(II)=0.67,
R$_F$(III)=0.66,
R$_F$(IV)=0.45,
R$_F$(V)=0.65
Amino acid analysis:
Asx 1.00 (1), Arg 1.85 (2)
Molecular weight determination:
C$_{22}$H$_{40}$N$_{12}$O$_{11}$ (648.6)
Elemental analysis:
Calculated: C 40.74 H 6.22 N 25.91; Found: C 40.70 H 6.40 N 25.79

XVII.4. Boc-Asn-Arg(NO$_2$)-Arg (NO$_2$)—OH

Boc-Asn-Arg(NO$_2$)-Arg(NO$_2$)-OMe (18.00 g, 27.75 mmol) in methanol (180 ml) was hydrolyzed with 1 N NaOH (80 ml) at room temperature. After 2 h, the mixture was neutralized with dilute HCl, and the methanol was removed by evaporation in vacuo. Exhaustive extraction with ethyl acetate was carried out at pH 3. The organic phases were washed with a little saturated NaCl solution, dried over Na$_2$SO$_4$ and the product was crystallized from a methanolic solution at −20 degrees Celsius.
Yield:
15.84 g (90%)
Melting point:
228 degrees Celsius (decomposition)
Thin-layer chromatography:
R$_F$(I)=0.49,
R$_F$(II)=0.21,
R$_F$(III)=0.26,
R$_F$(IV)=0.05,
R$_F$(V)=0.2

XVIII. Boc-Ala-Leu-Ile-Leu-Leu-Ala-Gln-(Ala-Aib-Ala-Aib-Ala)$_2$-OMe

XVIII.1 Boc-Ala-Aib-Ala-Aib-Ala—OH

Boc-Ala-Aib-Ala-Aib-Ala-OMe (10.03 g, 20 mmol) in MeOH (150 ml) was hydrolyzed with 1 N NaOH (40 ml, 40 mmol). After 2.5 hours, the mixture was neutralized with 1 N HCl, evaporated in vacuo and partitioned between EA/5% KHCO$_3$ (1:1; 1,000 ml). The aqueous phase was acidified to pH 4 with 5% KHSO$_4$ and was extracted five times with EA/1-butanol (5:1). The organic phase was dried over Na$_2$SO$_4$, PE (30–50) was added, and the pentapeptide acid was precipitated in the cold.
Yield:
6.54 g (65%)
Melting-point:
195 degrees Celsius (decomposition)

Thin-Layer chromatography
  $R_F(I)=0.72$,
  $R_F(II)=0.80$,
  $R_F(III)=0.87$,
  $R_F(IV)=0.95$,
  $R_F(V)=0.80$
Amino acid analysis:
  Ala 3.08 (3), Aib 1.98 (2)
Molecular weight:
  $C_{22}H_{39}N_5O_8$ (501.6)
Elemental analysis:
  Calculated: C 52.68 H 7.84 N 13.96; Found: C 52.70 H 7.90 N 13.89

XVIII.2. Boc-(Ala-Aib-Ala-Aib-Ala)$_2$-OMe

Boc-Ala-Aib-Ala-Aib-Ala—OH (1.75 g, 3.48 mmol) and HOBt (470 mg, 3.48 mmol) in DMF (10 ml) were added at −10 degrees Celsius to HCl×H-Ala-Aib-Ala-Aib-Ala-OMe (1.57 g, 3.48 mmol) and NMM (324 μl, 3.48 mmol) in DMF (8 ml). After addition of DCC (825 mg, 4.00 mmol) in $CH_2Cl_2$ (3 ml) at −10 degrees Celsius, the mixture was stirred for 15 h allowing it slowly to warm up spontaneously. After the reaction had been stopped with a few drops of glacial acetic acid, the DCU which had precipitated out was removed by centrifugation, the residue was washed twice with cold DMF, and the solvent was removed by evaporation in vacuo. The residue was taken up in 10 ml of $CHCl_3$/MeOH 1:1 and chromatographed on SEPHADEX LH 20 in $CHCl_3$/MeOH 1:1.
Yield:
  2.246 g (72%)
Melting point:
  160 degrees Celsius
Thin-layer chromatography:
  $R_F(I)=0.61$,
  $R_F(II)=0.76$,
  $R_F(III)=0.83$,
  $R_F(IV)=0.95$,
  $R_F(V)=0.81$
Molecular weight determination:
  $C_{40}H_{70}N_{10}O_{13}$ (899.1)
Elemental analysis:
  Calculated: C 53.44 H 7.85 N 15.58; Found C 53.42 H 7.90 N 15.40

XVIII.3. HCl×H-(Ala-Aib-Ala-Aib-Ala)$_2$-OMe

Boc-(Ala-Aib-Ala-Aib-Ala)$_2$-OMe (2.046 g, 2.276 mmol) was mixed with 1.2 N HCl/AcOH (10 ml). After stirring for 30 min, the hydrochloride was precipitated with ether, filtered off and dried over KOH under oil pump vacuum.
Yield:
  1.805 g (95%)
Thin-layer chromatography:
  $R_F(I)=0.50$,
  $R_F(II)=0.38$,
  $R_F(III)=0.71$,
  $R_F(IV)=0.48$,
  $R_F(V)=0.53$ XVIII.4. Boc-Gln-(Ala-Aib-Ala-Aib-Ala)$_2$-OMe Boc-Gln-OH (997 mg, 4.05 mmol) and HOBt (547 mg, 4.05 mmol) in DMF (10 ml) were added at −10 degrees Celsius to HCl ×H-(Ala-Aib-Ala-Aib-Ala)$_2$-OMe (2.250 g, 2.70 mmol) and NMM (298 μl, 2.70 mmol) in DMF (13 ml). After addition of DCC (846 mg, 4.10 mmol) in $CH_2Cl_2$ (2 ml) at −10 degrees Celsius, the mixture was stirred for 15 h allowing it slowly to warm up spontaneously. After the reaction had been stopped with a few drops of glacial acetic acid, the precipitated DCU was removed by centrifugation, the residue was washed twice with a little cold DMF, and the solvent was removed under oil pump vacuum. The residue was taken up in 10 ml of $CHCl_3$/MeOH 1:1 and chromatographed on SEPHADEX LH 20 in $CHCl_3$/MeOH (1:1).
Yield:
  2.60 g (94%)
Melting point:
  223 degrees Celsius (decomposition)
Thin-layer chromatography:
  $R_F(I)=0.66$,
  $R_F(II)=0.73$,
  $R_F(III)=0.79$,
  $R_F(IV)=0.94$,
  $R_F(V)=0.80$
Molecular weight determination:
  $C_{45}H_{78}N_{12}O_{15}$ (1027.2)
Elemental analysis:
  Calculated C 52.62 H 7.65 N 16.36; Found C 52.65 H 7.68 N 16.32

XVIII.5. HCL×H-Gln-(Ala-Aib-Ala-Aib-Ala)$_2$-OMe

Boc-Gln-(Ala-Aib-Ala-Aib-Ala)$_2$-OMe (2.60 g, 2.701 mmol) was mixed with 1.2 N HCL/AcOH (15 ml). After 40 min, the hydrochloride was precipitated with ether while stirring, removed by filtration and dried over KOH under oil pump vacuum.
Yield:
  2.209 g (85%);
Thin-layer chromatography:
  $R_F(I)=0.48$,
  $R_F(II)=0.25$,
  $R_F(III)=0.54$,
  $R_F(IV)=0.24$,
  $R_F(V)=0.35$ XVIII.6. Boc-Ala-Leu-Ile-Leu-Ala-Gln-(Ala-Aib-Ala-Aib-Ala)$_2$-OMe Boc-Ala-Leu-Ile-Leu-Leu-Ala—OH (760 mg, 1.07 mmol) and HOBt (145 mg, 1.07 mmol) in DMF (12 ml) were added at room temperature to HCl×H-Gln-(Ala-Aib-Ala-Aib-Ala)$_2$-OMe (818 mg, 0.85 mmol) and NMM (94 μl, 0.85 mmol) in DMF (10 ml). After addition of DCC (227 mg, 1.10 mmol) in $CH_2Cl_2$ (1.5 ml), the mixture was stirred for 64 h. After the reaction had been stopped with a few drops of glacial acetic acid, the precipitated DCU was removed by centrifugation, the residue was washed twice with a little cold DMF, and the solvent was removed under oil pump vacuum. The residue was taken up in 8 ml of $CHCl_3$/MeOH (1:1) and chromatographed on SEPHADEX LH-20 in $CHCl_3$/MeOH (1:1).
Yield:
  774 mg (57%)
Melting point:
  260 degrees Celsius (decomposition)
Thin-layer chromatography:
  $R_F(I)=0.80$,
  $R_F(II)=0.86$,
  $R_F(III)=0.91$,
  $R_F(IV)=0.77$,
  $R_F(V)=0.78$
Amino acid analysis:
  Gln 1.00 (1), Ile 0.86 (1), Leu 3.10 (3), Aib 4.08 (4), Ala 7.95 (8).
Molecular weight determination
  $C_{75}H_{132}N_{18}O_{21}$ (1622.0)
Elemental analysis
  Calculated C 55.54 H 8.20 N 15.54; Found C 55.58 H 8.31 N 15.52

XIX. Preparation of Boc-Asn-Arg(NO$_2$)-Arg(NO$_2$)-Ala-Leu-Ile-Leu-Ala-Gln-(Ala-Aib-Ala-Aib-Ala)$_2$-OMe

XIX.1. HCl×H-Ala-Leu-Ile-Leu-Leu-Ala-Gln-(Ala-Aib-Ala-Aib-Ala)$_2$-OMe

Boc-Ala-Leu-Ile-Leu-Leu-Ala-Gln-(Ala-Aib-Ala-Aib-Ala)$_2$-OMe (754 mg, 0.465 mmol) was mixed with 1.2 N HCl/AcOH (10 ml). After 50 min, the mixture was partly evaporated under oil pump vacuum and, after addition of water (10 ml), freeze-dried.
Yield
690 mg (95%)
Thin-layer chromatography:
R$_F$(I)=0.71,
R$_F$(II)=0.52,
R$_F$(III)=0.78,
R$_F$(IV)=0.56,
R$_F$(V)=0.54

XIX.2. Bos-Asn-Arg(NO$_2$)-Arg(NO$_2$)-Ala-Leu-Ile-Leu-Leu-Ala-Gln-(Ala-Aib-Ala-Aib-Ala)$_2$-OMe

Boc-Asn-Arg(NO$_2$)-Arg(NO$_2$)—OH (634 mg, 0.995 mmol) and HOBt (135 mg, 1.13 mmol) in DMF (5 ml) were added at −5 degrees Celsius to HCl×H-Ala-Leu-Ile-Leu-Leu-Ala-Gln-(Ala-Aib-Ala-Aib-Ala)$_2$-OMe (20 mg, 0.398 mmol) and NMM (44 microliters, 400 micromole) in DMF (7 ml). After addition of DCC (217 mg, 1.05 mmol) in CH$_2$Cl$_2$ (1.5 ml) at −5 degrees Celsius, the mixture was stirred for 48 h allowing it to warm up spontaneously. After the reaction had been stopped with 3 drops of glacial acetic acid, the precipitated DCU was removed by centrifugation. The working up and purification by chromatography were carried out as described previously.
Yield
630 mg (74%)
Melting point:
195 degrees Celsius (decomposition)
Thin-layer chromatography:
R$_F$(I)=0.70;
R$_F$(II)=0.51,
R$_F$(III)=0.56,
R$_F$(IV)=0.45,
R$_F$(V)=0.68
Amino acid analysis:
Asx 0.94 (1), Glx 1.00 (1), Ile 0.89 (1), Leu 3.16 (3), Arg 1.95 (2).
Molecular weight determination:
C$_{91}$H$_{160}$N$_{30}$O$_{29}$ (2138.5)
Elemental analysis:
Calculated C 51.11 H 7.54 N 19.65; Found C 51.14 H 7.60 N 19.66

XX. Preparation of the free eicosapeptide

XX.1. Boc-Asn-Arg-Arg-Ala-Leu-Ile-Leu-Leu-Ala-Gln-(Ala-Aib-Ala-Aib-Ala)$_2$-OMe×2HCl

Boc-Asn-Arg(NO$_2$)-Arg(NO$_2$)-Ala-Leu-Ile-Leu-Leu-Ala-Gln-(Ala-Aib-Ala-Aib-Ala)$_2$-OMe (350 mg, 0.164 mmol) in 3 ml of anhydrous methanol was mixed with 35 mg of Pd/active charcoal and 12 µl (0.075 mcol) of 6 N HCl. Hydrogen was passed through the solution while stirring at room temperature. After 20 min 8 µl (49 micromole), and after 35 min 7 µl (42 micromole), of 6 N HCl were added. After a hydrogenation time of about 50 min the cleavage off, as checked by TLC, was quantitative. The catalyst was removed by filtration and washed several times with a little Methanol. The solvent was rapidly removed by distillation in a rotary evaporator (oil pump vacuum, bath temperature 25 degrees Celsius), and the residue was taken up in a little water and freeze-dried.
Yield:
332 mg (95%)
Thin-layer chromatography:
R$_F$(I)=0.16,
R$_F$(II)=0.11,
R$_F$(III)=0.21,
R$_F$(IV)=0.10

XX.2. H-Asn-Arg-Arg-Ala-Leu-Ile-Leu-Leu-Ala-Gln-(Ala-Aib-Ala-Aib-Ala)$_2$-OMe×3HCl

Boc-Asn-Arg-Arg-Ala-Leu-Ile-Leu-Leu-Ala-Gln-(Ala-Aib-Ala-Aib-Ala)$_2$-OMe×2HCl (600 mg, 0.283 mmol) was mixed with 1.2 N HCl/AcOH (5 ml). After 30 min. the mixture was partly evaporated in a rotary evaporator, and the residue was mixed with water (10 ml) and freeze-dried.
Yield:
564 mg (97%)
Melting point:
245 degrees Celsius (decomposition)
Thin-layer chromatography:
R$_F$(I)=0.11
Molecular weight determination:
86$_{157}$N$_{28}$O$_{23}$Cl$_3$ (2057.7)
Elemental analysis:
Calculated C 50.20 H 7.69 N 19.06 Cl 5.17; Found C 50.31 H 7.78 N 18.95 Cl 5.28

Materials and Methods for the Above Experiments (examples I to XX)

Chemical

Analytical grade solvents were obtained from Merck, while other solvents were dried and distilled by customary methods. N-Methylmorpholine (Merck) was distilled over ninhydrin to remove sec. amines. 1-Hydroxybenzotriazole and dicyclohexylcarbodiimide likewise originated from Merck. All L-amino acid derivatives were obtained from Bachem. Boc-Aib-OH and H-Aib-OMe×HCl were synthesized by literature methods.

Thin-layer chromatography

Precoated silica gel 60 F$_{254}$ plates (supplied by Merck) and the following mobile phases were used:
(I) 1-Butanol/glacial acetic acid/water 3:1:1
(II) Chloroform/methanol/glacial acetic acid/water 65:25:3:4
(III) Chloroform/methanol/concentrated amonia/water 65:35:3:4
(IV) Chloroform/methanol/water 65:25:4
(V) Chloroform/methanol 1:1

The following spray reagents were used: ninhydrin reagent, chlorine/4,4'-bis(dimethylamino)diphenylmethane (TDM reagent) and Sakaguchi reagent. The reference used was dicyclohexylurea with the following values:
R$_F$(I) 0.91, R$_F$(II) 0.82, R$_F$(III) 0.92, R$_F$(IV) 0.81, R$_F$(V) 0.83.

Amino acid analyses

To establish the identity of the intermediates, approximately 200 microgram samples of each of the protected peptides were hydrolyzed in 6 N HCl at 110 degrees Celsius for 24 h. The intermediates and the target sequence of the hexapeptide segment which contains the Leu-Leu bond were hydrolyzed for 72 h under conditions which were otherwise identical. The amino acid analyses were carried out with a Biotronic LC 6000 E amino acid analyzer using the standard program.

Racemate determination:

The hydrolyzed amino acids were derivatized as the n-propyl esters of the pentafluoropropionylamino acid and the enantiomers were separated by gas chromatography on glass capillary columns with Chirasil-Val. The reported percentages of D-amino acids have not been corrected for racemization caused by the hydrolysis.

Elemental analyses

Single C, H and N-determinations were carried out using a model 1104 (Carlo Erba, Milan) elemental analyzer.

Melting points

Melting points were determined according to Tottoli and are uncorrected.

Recording of the spectra $^{13}$C NMR spectral: 30 mg of the protected eicosapeptide were dissolved in 400 microliters of $^{12}C^2HCl$ /$^{12}C^2H_3O^2H$ (1:1) (supplied by Merck) and measured in a WM 400 Bruker NMR spectrometer at 30° C. for 12 h. Circular dichroism spectra: solutions of the free eicosapeptide (c=1–1.7 mg/ml) in ethanol, trifluoroethanol, methanol, 1,1, 1,3,3,3-hexafluoro-2-propanol, water and ethanol/water mixtures were measured in a Dichrograph II (Jouhan-Roussel).

Purification by chromatography:

The protected peptide intermediates were, after termination of the coupling reaction and removal of the solvent under oil pump vacuum, dissolved by addition of the same volume of CHCl$_3$/MeOH 1:1, the dicyclohexylurea was removed by centrifugation, and the product was chromatographed on SEPHADEX LH 20: column 3×115 cm; eluting agent CHCL$_3$/MeOH 1:1; amount applied 35 ml; flow rate 8.40 ml/10 min. The 3 ml fractions were examined by thin-layer chromatography in system II (TDM reagent). The peptides appeared in the elution volume 165–190 ml. The fractions were combined; the solvent was removed in vacuo; and the residue was dried over P$_2$O$_5$. Amino acid analysis produced the expected values and a peptide content of 92–96%.

The following Example A demonstrates immunization tests, both in vivo and in vitro, mitogenic activation of mouse cells, and demonstrates a comparison of in vivo and in vitro tests:

EXAMPLE A

Immunization tests

We have for the first time covalently linked a B-cell mitogen, which is simultaneously an outstanding carrier and a highly active adjuvant, to synthetic antigenic determinants. For this we have used, inter alia, the synthetic lipopeptide S-(2,3-bis(palmitoyloxy)propyl)-N-palmitoylcysteinylserine (Pam$_3$Cys-Ser) which represents the N-terminal end of the lipoprotein from the outer membrane of *Escherichia coli*. The amphiphilic properties, which are particularly pronounced when covalently bonded to an antigen, ensure, on the one hand, stable anchoring of the S-glyceryl compound, which carries three fatty acid residues, in the lipid layer of the cell membrane. On the other hand, this means that the antigen (or hapten), which is usually more polar, is presented in the outer hydrophilic layer of the membrane. Since the activating effect of the lipoprotein is determined entirely by its N-terminal part, the immunostimulant effect of Pam$_3$Cys-Ser, or analogs, is retained in all the conjugates which carry it.

Figure 9:
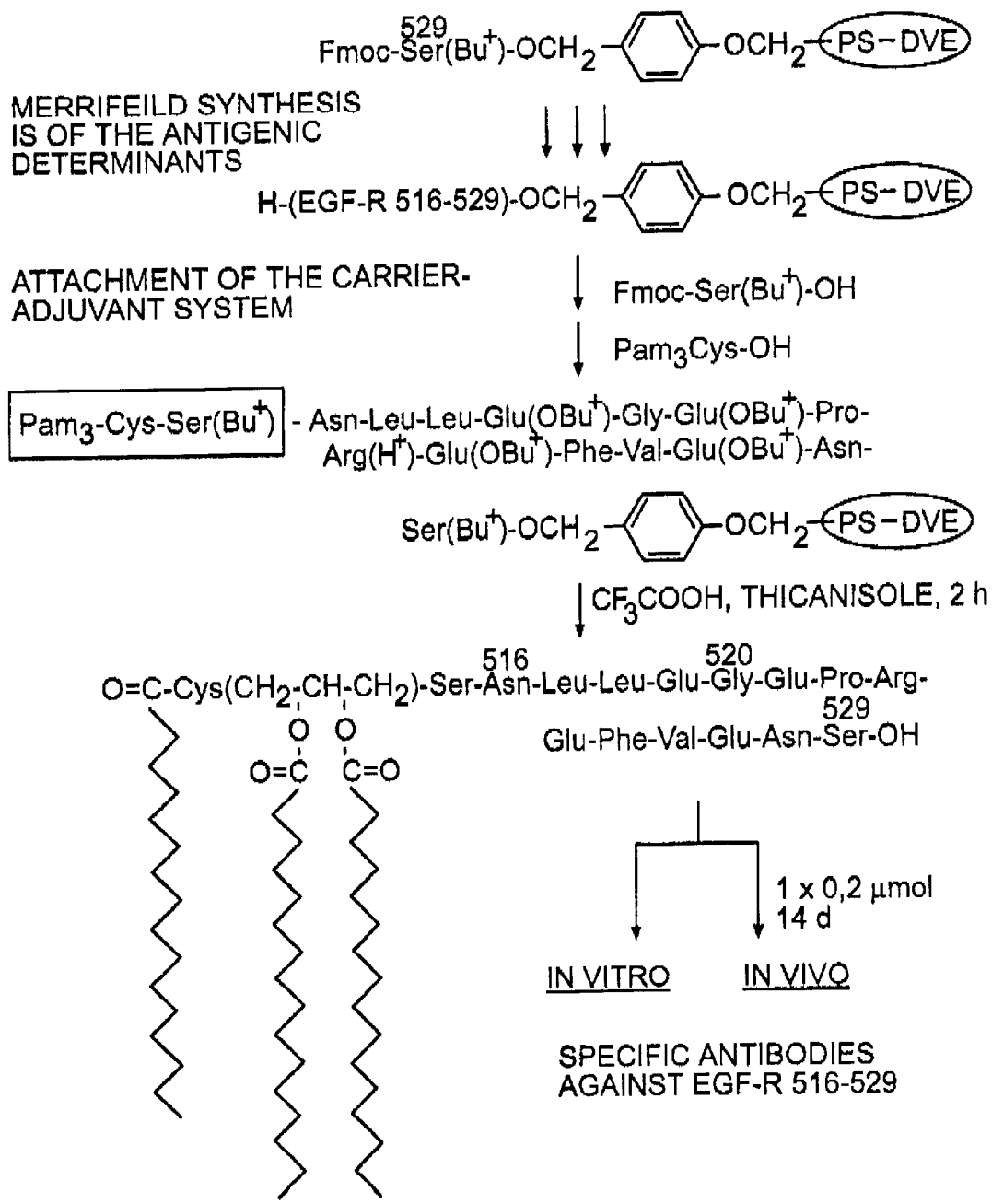
FIG. 9 the obtaining of antibodies using Pam$_3$Cys-Ser-EGF-R (516 to 529)

As an example, we detail the use of the concept for the generation of specific antibodies against epidermal growth factor receptor (EGF-R) FIG. 9. For this purpose, a computer-assisted search for epitopes led to selection of the extracytoplasmic region 516–529, which was constructed by Merrifield synthesis and finally Fmoc-Ser(But)—OH and then Pam$_3$Cys—OH were attached. The conjugate, which was found to be homogeneous by analysis, was cleaved off from the resin and then administered i.p., without further additives, in a single dose to mice. After only 2 weeks, sigh titers of specific antibodies against the tetradecapeptide were found by ELISAs. An essential point is that no antibody titers were obtained with the tetradecapeptide, which is by itself obviously a weak immunogen, in control experiments.

Since Pam$_3$Cys conjugates are likewise highly immunogenic in cell cultures, it is possible in a rapid and elegant manner to obtain conventional and monoclonal antibodies, even against weakly immunogenic compounds, by in vitro immunization.

The advantages of our concept in association with cell cultures are: straightforward preparation of a chemically unambiguously defined antigen-adjuvant conjugate in any desired amount, in contrast to other conjugates a single administration without multiple "boosters", and high efficiency in vivo and in vitro. The considerable saving in experimental animals, and frequently even dispensing completely with in vivo immunization and a drastic saving in time, especially in genetic engineering procedures, are obvious. The experiments can also be carried out with human cell culture systems.

Example of an in vivo immunizations 6- to 10-week old Balb/c mice were immunized by a single i.p. administration of 50 micrograms and 500 micrograms (0.2 ml of a $10^{-1}$ to $10^{-2}$ molar solution of adjuvant covalently coupled to antigen) of Pam$_3$Cys-Ser-(EGF-R 515–529). The controls used were antigen, adjuvant and a mixture of antigen and adjuvant, in each case in comparable molar amounts, and medium. Two weeks after the injection, blood was taken from the retroorbital venous plexus of the mice to obtain serum, and the antibody titer was determined by ELISA.

Analogous immunizations can also be obtained by other administrations, for example, i.v., oral, rectal, i.m. and s.c.

The formation of specific antibodies without Freund's adjuvant against the tetradecapeptide EGF-R 516–529 after in vivo immunization was examined.

Balb/c mice were immunized once i.p. with 0.2 micromol of the conjugate

I. Conjugate Pam$_3$Cys-Ser (EGF-R 516–529)

II. Free tetradecapeptide EGF-R 516–529 alone

III. Pam$_3$Cys-Ser alone

Figure 10:
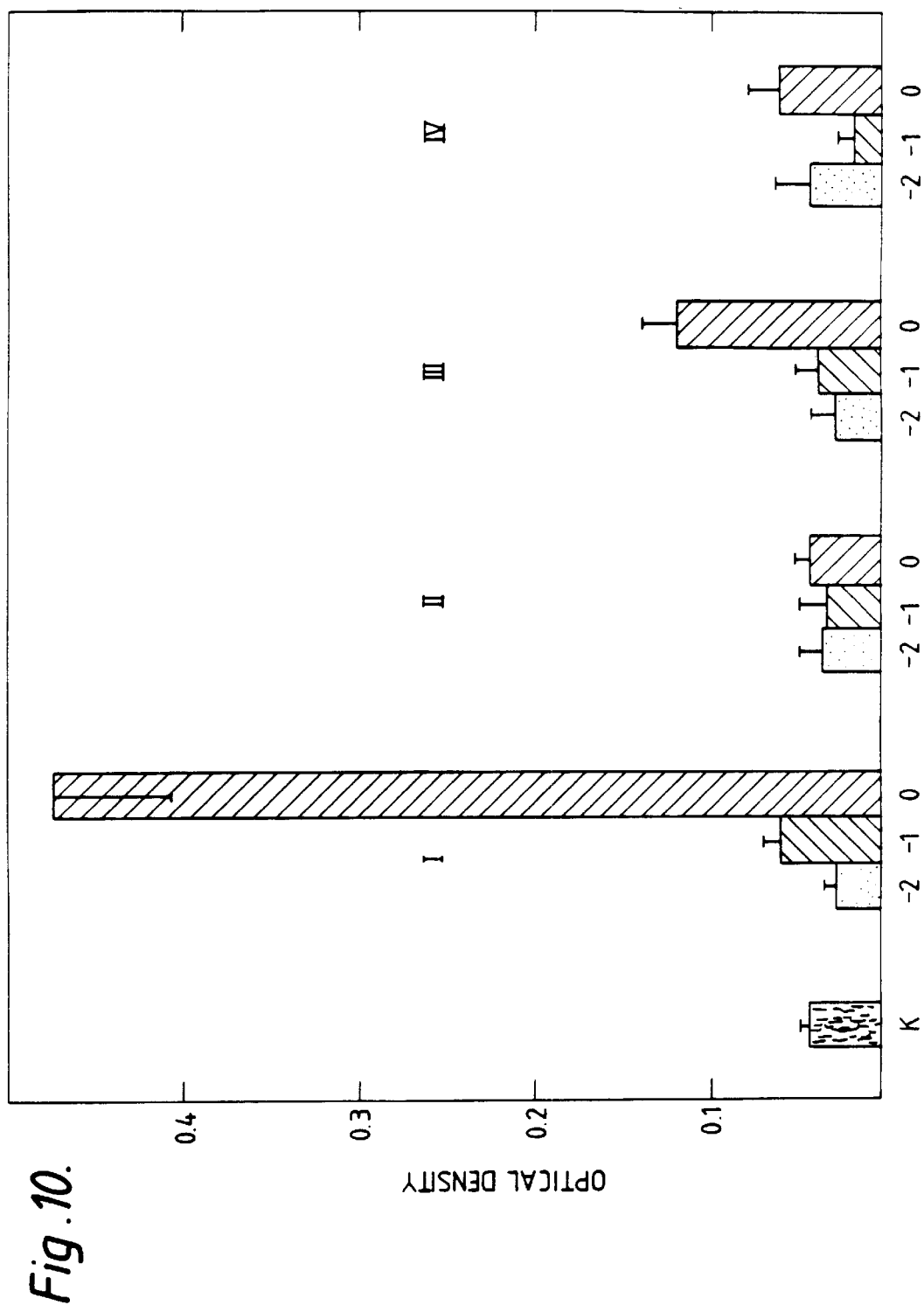
FIG. 10 an in vivo immunization experiment.

IV. Free tetradecapeptide (EGF-R 516–529) mixed together with Pam$_3$Cys-Ser as shown in FIG. 10. The antibody titer was determined by ELISA. (Ordinate OD at 405 nm) (FIG. 10).

14 days after the immunization the mice were bled from the ophthalmic vein, and the serum which was obtained was used in ELISA. The values emerge from the mean (3–5 mice) of the difference between the ELISA values of PEP 14—BSA conjugate and BSA (FIG. 10).

It is evident that only when the membrane anchor/active compound conjugate according to the invention is used are drastically elevated antibody concentrations, which exceed the activity of those with previous processes by a multiple, found.

Example of an in vitro immunization:

Samples of mouse spleen cells were cultivated for 5 days in the presence of the conjugate Pam$_3$Cys-Ser-(EGF-R 516–529), of the adjuvant Pam$_3$Cys-Ser, of the tetradecapeptide EGF-R 516–529, of a mixture of the antigen and adjuvant, and of medium.

The lymphocytes were cultivated at a cell density of $2.5 \times 10^6$/ml in 0.2 ml aliquot in RPMI-1640 medium enriched with 10% heat-inactivated FCS, glutamine (2 mM), penicillin (100 U/ml), streptomycin (100 µg/ml) and 2-mercaptoethanol ($5 \times 10^{-5}$ M), for 48 h.

The supernatants were obtained for examination for specific antibodies by ELISA.

Figure 12:
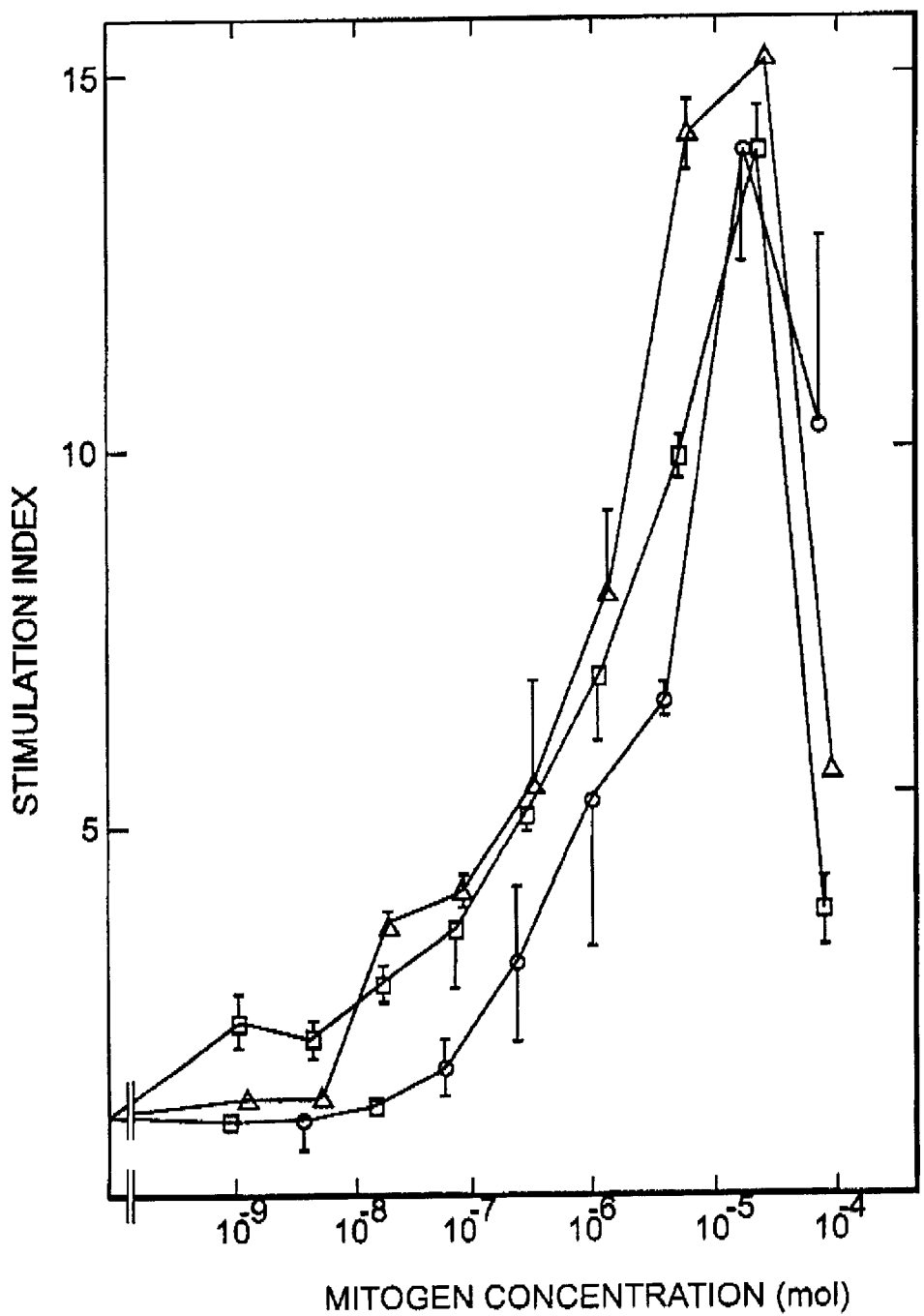
FIG. 12 the mitogenic activation of Balb/c mouse spleen cells using Pam$_3$Cys-Ser-(Lys)$_4$FITC.

Mitogenic activation of mouse spleen cells:

The mitogenic activation of Balb/c spleen cells by $Pam_3$-Cys-Ser-$(Lys)_4$-FITC (circles), $Pam_3$Cys-Ser-$(Lys)_4$-OH× 3HCl (triangles) and $Pam_3$Cys-Ser-$(Lys)_4$-OH×2 TFA (squares) is shown in FIG. 12. The cell cultivation conditions have been described (Z. Immunforsch. 153, 1977, pp. 11 et seq. and Eur. J. Biochem. 115, 1981). In the figure, the stimulation index for the incorporation of $^3$H-thymidine into the DNA (cpm for incorporation/cpm for the control without mitogen) is plotted as the ordinate against the concentration of active compound used.

Figure 11:
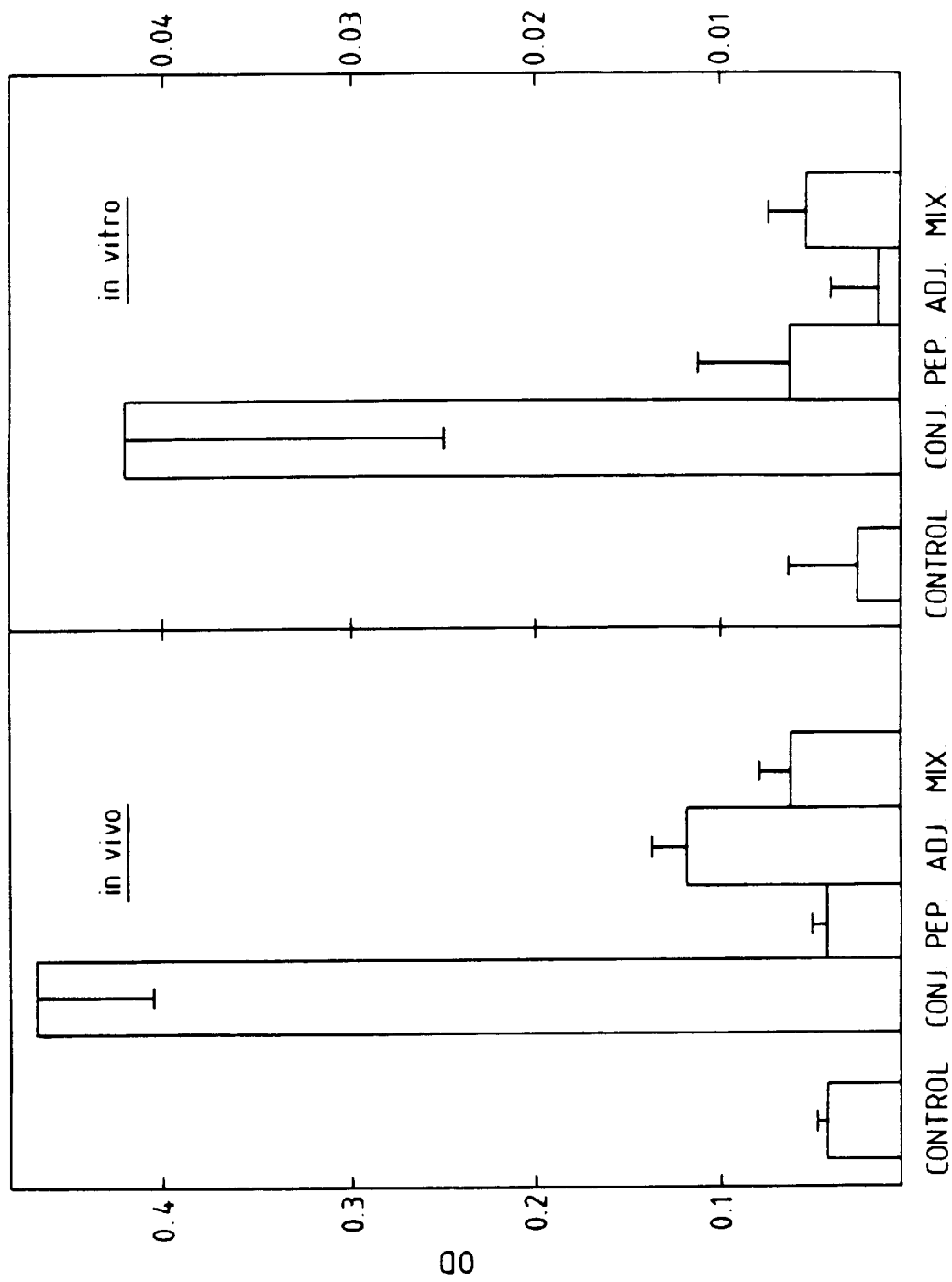
FIG. 11 a comparison of the in vivo and in vitro immunization experiments.

In vivo/in vitro comparison:

In FIG. 11 the in vivo experiment detailed above is compared with an in vitro experiment: In vitro experiment in microtiter plates: cell density: $2.5 \times 10^6$ cells/ml; substance concentration: $5 \times 10^{-7}$ millimolar; incubation conditions: 37° C., 5% $CO_2$, 5 days.

Conj.: conjugate $Pam_3$Cys-Ser-(EGF-R 516–529)
Pep: tetradecapeptide EGF-R 516–529
Adj.: $Pam_3$Cys-Ser
Mix: mixture of free tetradecapeptide EGF-R 516–529 and $Pam_3$Cys-Ser.

The drastic rise in the antibody concentration also emerges in vitro, and this considerably extends the utilizability of cell cultures, in particular for the preparation of antibodies.

The Examples that follow (Examples 1–7) illustrate the particular aspects of the invention which relate to the vaccine against foot and mouth disease, the synthetic vaccine for the specific induction of cytotoxic T-lymphocytes, and the processes for their preparation:

Example 1

Conjugation of peptides/proteins with $Pam_3$Cys-Ser-Ser-OSu or $Pam_3$Cys-Ser-Ser—OH 1. Peptides and proteins soluble in DMF 2 μmol of peptide/protein are dissolved in 0.5–1 ml of DMF, and 8 μmol (9.2 mg) of solid $Pam_3$Cys-Ser-Ser-OSu are added.

A homogeneous solution is obtained by gentle heating and sonication, and 4 μmol of organic base (N-ethylmorpholine) are added. After stirring for 12 h, 1–2 ml of chloroform: methanol (1:1) are added, and the mixture is cooled in an ice bath for 2 h.

The sediment is taken up with 1 ml of cold chloroform:methanol (1:1) washed in tert.butanol/water (3:1) (sonicate if necessary) and freeze-dried.

2. Peptides and proteins soluble in water

2 μmol of peptide/protein are dissolved in 0.8 ml of water, and 4 μmol (4.5 mg) $Pam_3$Cys-Ser-Ser—OH are added. The mixture is thoroughly sonicated until an emulsion is produced and a pH of 5.0 to 5.5 is set up. After 5 mg of EDC (1-3-dimethylaminopropyl)-3-ethylcarbodiimide hydrochloride) dissolved in 100 μl of $H_2O$ has been added, the mixture is stirred at room temperature for 18 h and then dialyzed twice against 1 l of distilled $H_2O$ each time. The contents of the dialysis tube are freeze-dried.

Example 2

Separation of the diastereomers of N-palmitoyl-S-(2,3-(bispalmitoyloxy)propyl]-cysteine tert.-butyl ester ($Pam_3$cys-OBu$^t$):

2 g of $Pam_3$Cys-OBu$^t$ are dissolved in 10 ml of mobile phase, dichloromethane/ethyl acetate (20:1), and loaded onto a column (length 120 cm, diameter 4 cm) packed with MN silica gel 60, 0.063–02 mm/70–230 mesh ASTM. At a drop rate of 2 drops/sec, 350 fractions each of 10 ml are collected, and an aliquot of each fraction is checked for $Pam_3$Cys-OBu$^t$ after chromatography on silica gel 60 plates in dichloromethane/ethyl acetate (20:1) and staining with chlorine/TDM reagent.

Fractions 280–315 contain the R,R diastereomer, fractions 316–335 contain a mixture of R,R and R,S, and fractions 336–354 contain the R,S diastereomer of $Pam_3$Cys-OBu$^t$. After the solvent has been evaporated off in a rotary evaporator and the residue has been taken up in warm tert.-butanol and freeze-dried, 600 mg of R,R-, 370 mg of a mixture of R,R- and R,S-, and 540 mg of R,S-$Pam_3$Cys-OBu$^t$ are obtained.

Example 3

Synthesis of N-palmitoyl-S-[2,3-(bispalmitoyloxy)propyl]-cysteinyl-seryl-seryl-VP 1 (135–154)

The VP 1 peptide sequence of FMD virus serotype $O_1K$ was synthesized by solid-phase peptide synthesis. Fmoc-amino acids were used. The following side-chain protective groups were used: Lys(Boc), His(Fmoc), Arg(Mtr), Ser (tBu), Asp(OtBu), Tyr(tBu). Starting from 1 g of (p-benzoyloxybenzyl alcohol)-resin loaded with Fmoc-Lys (Boc)—OH, (0.47 mmol/g), the following synthesis cycles were performed:

N-Activation with 55% piperidine in N-methylpyrrolidone (1×2 min, 1×5 min), preactivation of Fmoc-A—A—OH (1.5 mmol) in N-methylpyrrolidone (6 ml) with diisopropylcarbodiimide (1.5 mmol) and 1-hydroxybenzotriazole (1.5 mmol) with subsequent coupling for 1.5 h. Washing with N-ethylmorpholine (5% in N-methylpyrrolidone) was followed by repetition of the preactivation and coupling. The blocking of unreacted amino groups was carried out with acetic anhydride (2.5 mmol) and diisopropylamine (1.2 mmol) in N-methylpyrrolidone. After each step, the peptide-resin was washed several times with N-methylpyrrolidone, dichloromethane and again with N-methylpyrrolidone.

After the resin-bound FMD virus sequence had been synthesized, a part of the peptide was obtained by cleavage with trifluoroacetic acid and checked by HPLC, MS, amino acid analysis, chiral phase analysis and sequence analysis. The bonding of 2 serine residues to the resin-bound peptide was followed by Coupling of the tripalmitoyl-S-glycerylcysteine. After 4 hours, 1 equivalent of N-methylmorpholine was added, and after another hour the lipopeptide-resin was washed. The lipopeptide was separated from the resin using 2 ml of trifluoroacetic acid (containing 100 μl of thioanisole) within 4½ hours. The filtrate was evaporated, the residue was taken up with acetic acid, and the solution was added to cold ether. The precipitated lipopeptide was washed 3× with ether. Further purification was achieved by recrystallization from trifluoroethanol/chloroform in the ratio 1:3 with cold acetone and a few drops of water. The lipopeptide was freeze-dried from tert.-butanol/water in the ratio 3:1.

Example 4

Activity test:

Guinea pigs with a weight of 450 to 500 g chosen at random were inoculated intramuscularly or subcutaneously. 0.5 mg of the freeze-dried vaccine (N-palmitoyl-S-[(2R,R)-2,3-(bispalmitoyloxy) propyl]-cysteinyl-seryl-seryl-VP1 (135–154)) was emulsified in 500 μl of a 1:1 mixture of 0.05

M phosphate buffer and Intralipid$^{(R)}$ (Kabi Vitrum, Sweden). The mixture was sonicated for 10 s. Four animals were infected with FMD virus by subcutaneous injection into the left rear paw of at least 500 guinea pigs units of a virulent O$_1$K FMD virus 21 days after the inoculation. Control animals were injected with the membrane-anchoring compound or phosphate buffer in place of the vaccine. A high titer of neutralizing antibodies log$_{10}$SN$_{50}$ of 0.36 was found in all the inoculated animals. The control animals had no antibody titer (blank 0.17). The titer of neutralizing antibodies was determined as the logarithm of the serum dilution necessary to neutralize 50% of the virus cells in a monolayer of BHK (baby hamster kidney) cells. It was possible to detect antibodies in the inoculated animals by means of an anti-peptide ELISA (A$_{492}$), which was not possible for the non-inoculated animals. Inoculated animals showed no secondary lesions, whereas all the non-inoculated animals showed the complete picture of foot and mouth disease infection.

Example 5

Synthesis of N-palmitoyl-S-[2,3(bispalmitoyloxy)-propyl)-cysteinyl-seryl-seryl-NP 147–15

The influenza A virus nucleoprotein peptide sequence was synthesized by solid phase peptide synthesis. Fmoc-amino acids were used. The following side chain-protecting groups were used: Thr(tBu), Tyr(tBu), Arg(Pmc). 1 g of para-benzyloxybenzyl alcohol resin to which 0.5 mmol of Fmoc-Gly were bound, was used and the peptide sequence was synthesized by the following synthesis cycles. N-activation by 50% piperidine in DMF (1×10 min). Coupling of the subsequent amino acid for 30 min. using BOP/HOBT (benzotriazol-1-yl-oxy-tris-(dimethylamino)-phosphonium hexafluorophosphate/1-hydroxybenzotriazole] and diisopropylethylamine in DMF. Double couplings were carried out in each case using a 3-fold excess of Fmoc-amino acid and 4.5-fold excess of diisopropylethylamine (in each case in relation to free amino groups on the resin). After each double coupling the peptide resin was washed, in each case, three times with N-methylpyrrolidone, dichloromethane and N-methylpyrrolidone.

After the synthesis of the resin-bound influenza A virus nucleoprotein sequence, part of the peptide was isolated by cleavage with trifluoroacetic acid and tested for purity by means of HPLC, MS, amino acid analysis, analysis on chiral phase and sequence analysis. The HPLC analysis revealed a purity of more than 90%. After coupling two serine residues [Fmoc-Ser(tBu)] to the resin-bound peptide, the coupling of the tripalmitoyl-S-glycerolcysteine was carried out by the DIC/HOBT method. After four hours, one equivalent of N-methylmorpholine was added and, after one further hour, the lipopeptide-resin was washed. The lipopeptide was separated from 100 mg of resin by means of 2 ml of trifluoroacetic acid (containing 100 μl of thioanisole and 100 μg of thiocresol) in the course of one hour. In order to completely remove the Arg(Pmc) protecting groups, an additional treatment with trifluoroacetic acid was carried out at 50° C. for 30 minutes. The filtrate was evaporated, the residue taken up in acetic acid and added to cold ether. The precipitated lipopeptide was washed three times with ether and freeze-dried from tert.-butanol/water in a ratio of 3:1.

Example 6

Synthesis of N-palmitoyl-S-[2,3-bispalmitoyloxy)-propyl]-cysteinyl-seryl-seryl-NP (365–380)

The synthesis was carried out in analogy to Example 5. Fmoc-amino acids with the following side chain-protecting groups were used: Ser(tBu), Glu(OtBu), Thr(tBu). Asn was coupled with a side chain-protecting group by means of diisopropylcarbodiimide/HOBT. The initial resin used was Fmoc-Glu(OtBu)-p-benzyloxybenzyl alcohol-polystyrene, cross-linked with 1% divinylbenzene. The amount of Fmoc-Glu(OtBu) found was 0.45 mmol/g. The peptide and Pam$_3$Cys-Ser-Ser peptide was cleaved off from, in each case, 100 mg of resin using 2 ml of trifluoroacetic acid with the addition of 0.1 ml of thioanisole and 100 μg of thiocresol, in the course of 90 minutes. The sequence was confirmed by sequence analysis of the free peptide; a homogeneous peak containing more than 90% was determined by HPLC analysis. Amino acid analysis and testing for enantiomeric purity on chiral phase had the expected values as a result.

Example 7

Activity tests

A) 3-month-old BALB/c inbred mice which had been bred under SPF conditions were immunized intravenously with 100 μg of Pam$_3$Cys-Ser-Ser-[NP 147–158]. (100 μg of Pam$_3$Cys-Ser-Ser-]NP 147–158], taken up in 300 μl of PBS, sonicated for 1 minute). After 28 days, the mice were infected intranasally with 0.2 or 0.4 hemagglutinative units of influenza virus A/PR/8. In analogy, mice with 300 μl of PBS were administered intravenously and were infected as a control. The course of the infection was monitored by means of daily controls of weight and by the survival rate. 11 of 12 control animals which had been infected with 0.4 hemagglutinative units died from the virus infection after 11 days while only 4 of the 12 immunized animals died.

A further control group and a group immunized with Pam$_3$Cys-Ser-Ser-[NP 147–158] were infected with 0.2 hemagglutinative units of influenza virus. After 18 days, 40% of the control animals (4 of 10 animals) were still alive while 75% of the immunized animals were alive. On day 18 the weight difference between immunized animals and control animals was 4 g. The surviving animals of the control group continued to lose weight while the immunized animals slowly recovered from the infection.

B) Cytotoxic T-cell activity of spleen cells from BALB/c mice after immunization with free peptide, virus or Pam$_3$Cys-Ser-Ser-peptide (FIG. 13) BALB/c mice received by intravenous administration in 300 μl of PBS a) 8×10$^7$ syngeneic spleen cells preincubated with 1.6 μM of nucleoprotein peptide 147–158 (R-); (FIGS. 13: A, D, G), b) 8×10$^7$ syngeneic spleen cells preincubated with 160 μM of Pam$_3$Cys-Ser-Ser-[NP 147–158 (R-)] lipopeptide; (FIGS. 13: C, F), c) 50 hemagglutinative units of influenza A virus PR/8/34; (FIGS. 13: B, E, H), d) 100 μg of Pam$_3$Cys-Ser-Ser-[NP 147–158 (R-)]; (FIGS. 13: I).

Figure 13:
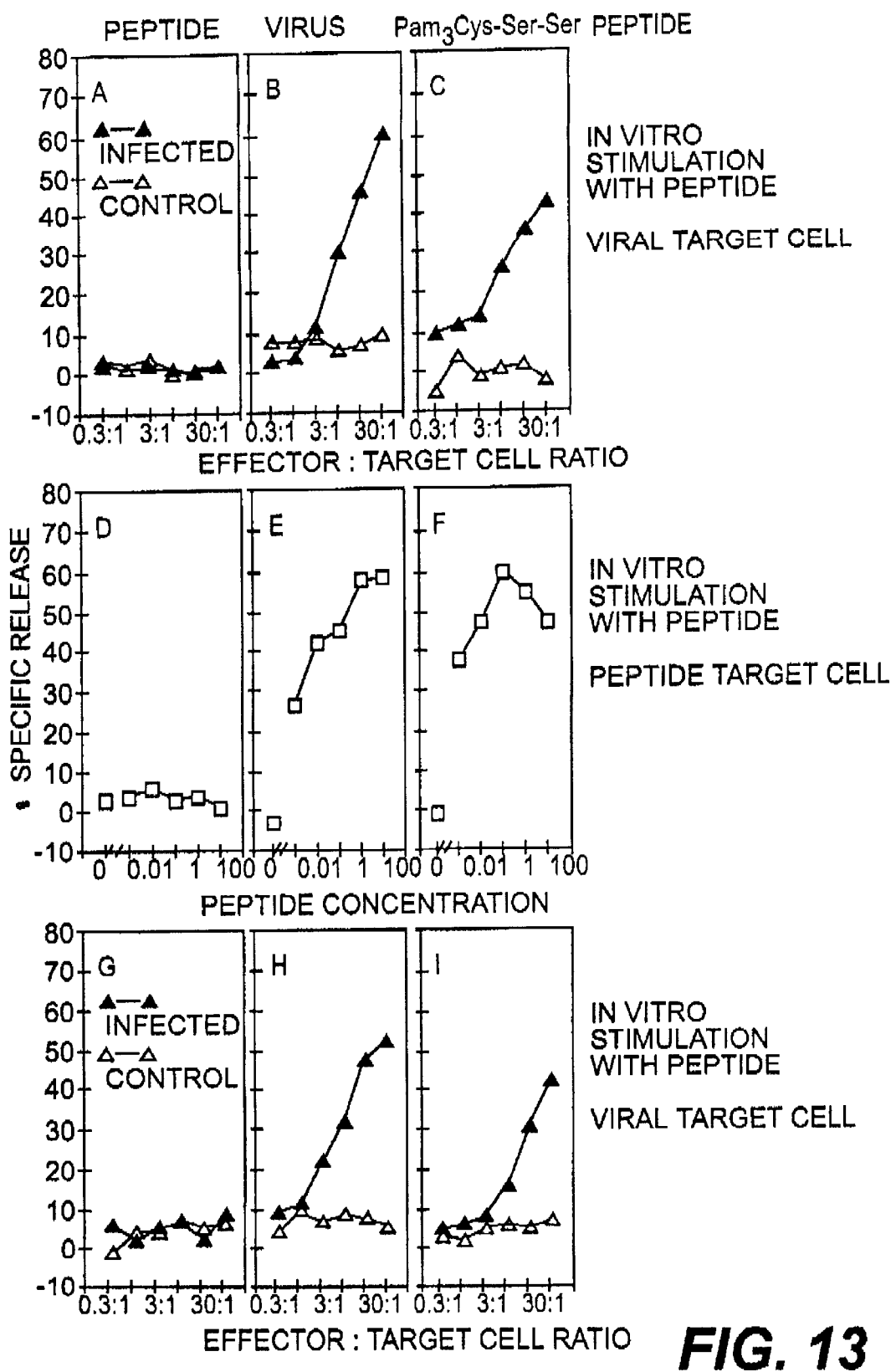
FIG. 13 the cytotoxic T-cell activity of spleen cells from BALB/c mice after immunization with free peptide, virus or Pam$_3$Cys-Ser-Ser-peptide.

After 6 days, the spleens were removed from the immunized or infected animals and these spleen cells were restimulated with peptide (FIGS. 13: A to F) or with syngeneic stimulator cells infected with virus PR8 (FIGS. 13: G, H, I) for 5 days. For this purpose, 2.5×10$^7$ cells in each case were cultivated in 10 ml of a-MEM medium (manufacturer: Gibco), supplemented with 10% fetal calf serum, 2-mercaptoethanol, glutamine and antibiotics with the addition of either 80 nM of NP 147–158(R-) peptide (FIGS. 13: A, F) or of 5×10$^6$ virus PR8-infected, syngeneic spleen cells which have been irradiated with 20 Gy (FIGS.

13: G, H, I). The infection of the stimulator and target cells was carried out as described (Eur. J. Immunol. 7, 630–635 (1977)).

The activity of the cytotoxic T-cells was determined by a $^{51}$Cr-release standard test (Eur. J. Immunol. 137, 2.676–2.681 (1986)). FIGS. 13: A, B, C and G, H, I show the CTL activity on untreated (Δ) or PR8-infected (▲) P815 (MHC:H-2$^d$) target cells.

FIGS. 13: D, E and F show CTL activity on P815 cells which were treated with various concentrations of free peptide at 37° C. for 30 minutes. In this case, a ratio of effector to target cell of 30:1 was used.

Figure 14:
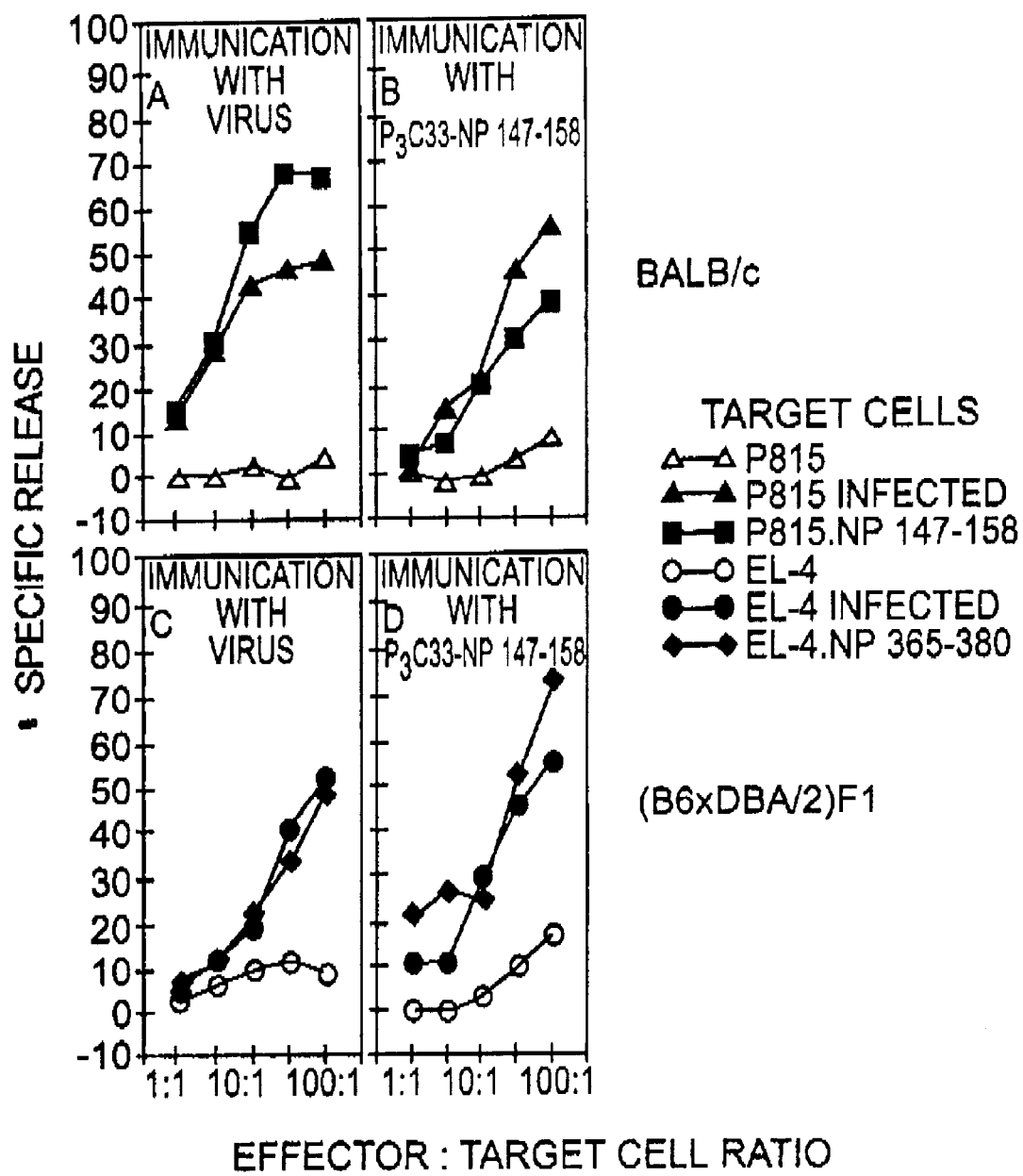
FIG. 14 the activity of cytotoxic T-cells after immunization of mice with Pam3 Cys-Ser-Ser-[NP 147–158] or Pam$_3$Cys-Ser-Ser-[NP 365–380]

C) Activity of cytotoxic T-cells after immunization of mice with Pam$_3$Cys-Ser-Ser-[NP 147–158] or Pam$_3$Cys-Ser-Ser-[NP 365–380] (FIG. 14)

BALB/c mice (FIGS. 14: A, B) or (B6×DBA/2) F1-mice (FIGS. 14: C, D) were immunized with influenza A virus (FIGS. 14: A, C) or with 100 μg of Pam$_3$Cys-Ser-Ser-[NP 147–158] (FIG. 14: B) or with 100 μg of Pam$_3$Cys-Ser-Ser-[NP 365–380] (FIG. 14: D). After 6 days, the spleens were removed and the spleen cells were, as described under FIG. 14: B), stimulated in the presence of 0.8 μM of NP 147–158 peptide (FIGS. 14: A, B) or 0.8 μM of NP 365–380 peptide (FIGS. 14: C, D). The activity of the cytotoxic T-cells on untreated P815 target cells (Δ), on PR8-inflected P815 target cells (▲) and on P815 target cells preincubated with NP 147–158 peptide at 37° C. for 90 minutes (■) was then assayed; likewise on untreated EL-4-(MHC H-2$^d$) cells (○), on PR8-inflected EL-4 target cells (●) and on EL-4 cells preincubated with NP 365–380 peptide at 37° C. for 90 minutes (◆).

Figure 15:
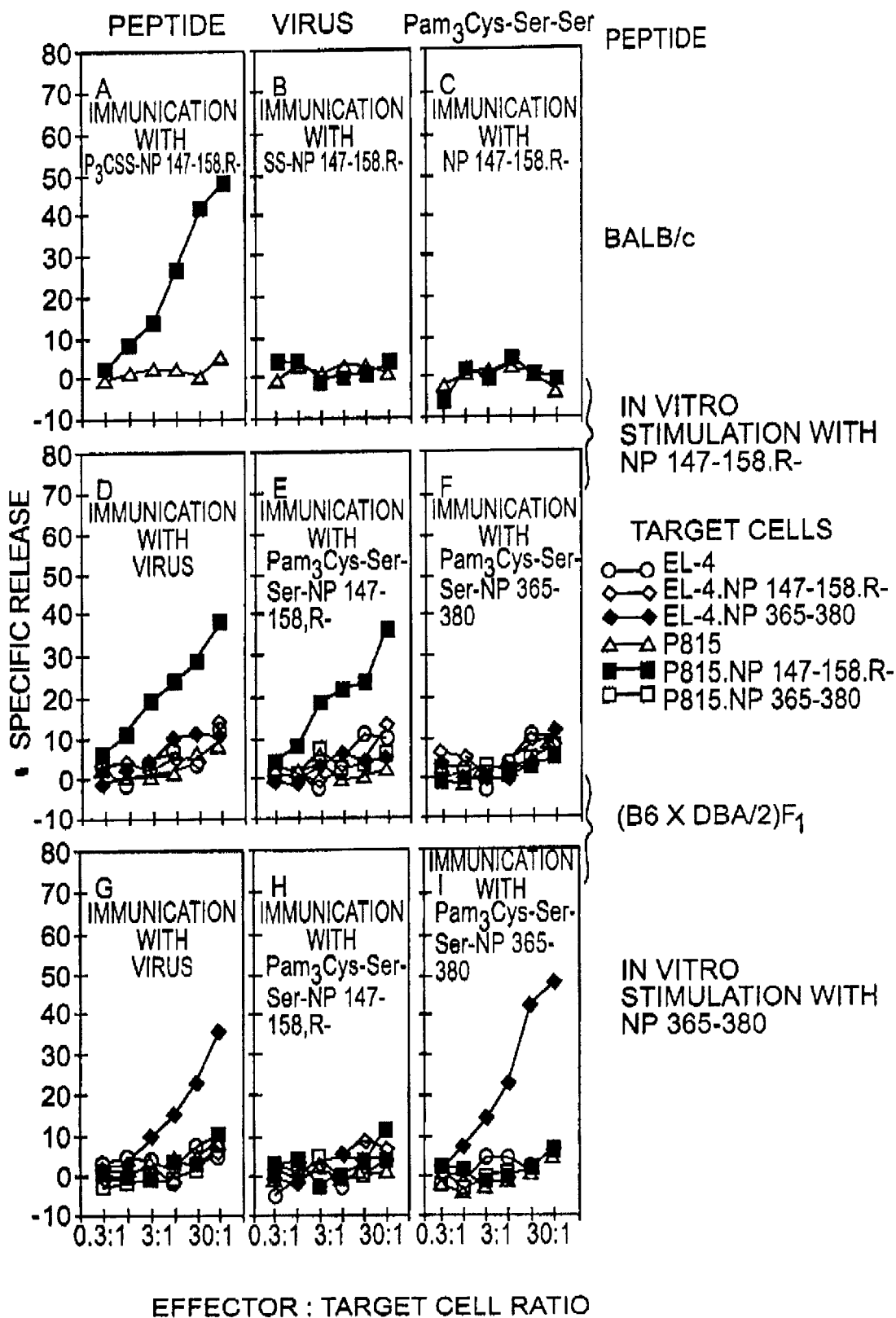
FIG. 15 the test for MHC class I restriction and for specificity of the immunization with lipopeptide.

D) Test for MHC class I restriction and for specificity of the immunization with lipopeptide (FIG. 15)

BALB/c mice (FIGS. 15: A, B, C) or (B6×DBA/2) F1-mice (FIGS. 15: D-I) received i.v. in 300 μl of PBS 100 μg of Pam$_3$Cys-Ser-Ser-[NP 147–158(R-)] (FIGS. 15: A, E, H) or 50 μg of Ser-Ser-[NP 147–158(R-)] (FIG. 15: B) or 50 μg of [NP 147–158(R-)] (FIG. 15: C) or 50 hemagglutinative units of influenza PR8 virus (FIGS. 15: D, G) or 100 μg of Pam$_3$Cys-Ser-Ser-[NP 365–380] (FIGS. 15: F, I).

Six days after the injection, the spleen cells were cultivated, as described in Example 2, with the addition of nucleoprotein 147–158(R-) peptide (FIGS. 15: A–F), or nucleoprotein 365–380 peptide (FIGS. 15: G–I). The activity of the resulting cytotoxic T-cells was determined against untreated P815 target cells (Δ)

P815 target cells preincubated with NP 147–158(R-) at 37° C. for 90 minutes (■)

P815 target cells preincubated with NP 365–380 at 37° C. for 90 minutes (□)

untreated EL-4 target cells (○)

EL-4 target cells preincubated with NP 147–158(R-) at 37° C. for 90 minutes (◇)

CL-4 target cells preincubated with NP 365–380 at 37° C. for 90 minutes (◆).

We claim:

1. A method for making an antibody specific for an antigenic material which includes an antigenic determinant, said method comprising administering to an antibody-producing source an effective amount of a membrane anchor/active compound conjugate having the following formula I:

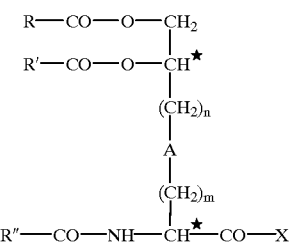

wherein A is sulfur, oxygen, disulfide (—S—S—), methylene (—CH$_2$—) or —NH—; n is 0 to 5; m is 1 or 2, CH* is an asymmetric carbon atom with R or S configuration; R, R', and R" are identical or different and are an alkyl, alkenyl, or alkynyl group having 7 to 23 carbon atoms, which can be substituted by hydroxyl, amino, oxo, acyl, or cycloalkyl groups, and X is the antigenic material.

2. A method as claimed in claim 1, wherein the compound of formula I is Pam$_3$Cys-X or Pam$_3$Cys-Ser-X.

3. A method as claimed in claim 1, wherein the antigenic material is selected from a low molecular weight partial sequence of a protein or a conjugated protein.

4. A method as claimed in claim 3, wherein the protein or conjugated protein is a viral coat protein, a bacterial cell wall protein, or a protein of protozoa.

5. A method as claimed in claim 3, wherein the protein or conjugated protein is a glycoprotein.

6. A method as claimed in claim 1, wherein the antigenic material is a constituent of a bacterial membrane.

7. A method as claimed in claim 6, wherein the constituent of a bacterial membrane is a lipopolysaccharide.

8. A method as claimed in claim 1, wherein

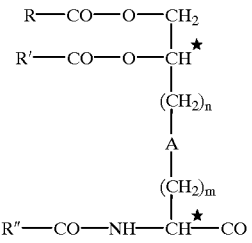

is a Pam$_3$Cys-peptide having 1 to 10 amino acids.

* * * * *